United States Patent
Davies et al.

(10) Patent No.: US 7,645,775 B2
(45) Date of Patent: Jan. 12, 2010

(54) TRIAZOLES USEFUL AS INHIBITORS OF PROTEIN KINASES

(75) Inventors: Robert Davies, Somerville, MA (US); Cornelia Forster, Pelham, NH (US); Michael Arnost, North Andover, MA (US); Jian Wang, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 352 days.

(21) Appl. No.: 11/255,569

(22) Filed: Oct. 21, 2005

(65) Prior Publication Data

US 2007/0270410 A1    Nov. 22, 2007

Related U.S. Application Data

(60) Provisional application No. 60/621,270, filed on Oct. 21, 2004.

(51) Int. Cl.
| | |
|---|---|
| *A61K 31/551* | (2006.01) |
| *A61K 31/5377* | (2006.01) |
| *A61K 31/496* | (2006.01) |
| *A61K 31/4523* | (2006.01) |
| *C07D 413/14* | (2006.01) |
| *C07D 243/08* | (2006.01) |

(52) U.S. Cl. ............... 514/318; 514/254.05; 514/236.2; 514/218; 540/575; 544/366; 544/364; 544/112; 546/194

(58) Field of Classification Search ............. 514/236.2, 514/218, 254.05, 318; 540/575; 544/112, 544/364, 366; 546/194
See application file for complete search history.

(56) References Cited

U.S. PATENT DOCUMENTS

| | | | |
|---|---|---|---|
| 7,226,920 B2 * | 6/2007 | Arnost et al. ............. 514/236.2 |
| 7,279,469 B2 * | 10/2007 | Pierce et al. ............ 514/217.09 |
| 2005/0182116 A1 | 8/2005 | Ronghui et al. ............. 514/383 |

FOREIGN PATENT DOCUMENTS

| | | |
|---|---|---|
| WO | WO 02/057240 A1 | 7/2002 |
| WO | WO 02/094814 A1 | 11/2002 |
| WO | WO 2004/046120 A2 | 3/2004 |
| WO | WO 2005/013982 A1 | 2/2005 |

* cited by examiner

*Primary Examiner*—Rebecca L Anderson
*Assistant Examiner*—Jason Nolan
(74) *Attorney, Agent, or Firm*—Daniel A. Pearson

(57) ABSTRACT

The present invention relates to inhibitors of protein kinases. The invention also provides pharmaceutical compositions comprising the compounds of the invention and methods of using the compositions in the treatment of various disorders.

12 Claims, No Drawings

TRIAZOLES USEFUL AS INHIBITORS OF PROTEIN KINASES

This application claims benefit of U.S. Provisional Application 60/621,270, filed Oct. 21, 2004, which is herein incorporated by reference in its entirety.

TECHNICAL FIELD OF THE INVENTION

The present invention relates to inhibitors of protein kinases. The invention also provides pharmaceutical compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

A family of type III receptor tyrosine kinases including Flt3, c-Kit, PDGF-receptor and c-Fms play an important role in the maintenance, growth and development of hematopoietic and non-hematopoietic cells. [Scheijen, B, Griffin J D, *Oncogene*, 2002, 21, 3314-3333 and Reilly, J T, *British Journal of Haematology*, 2002, 116, 744-757]. FLT-3 and c-Kit regulate maintenance of stem cell/early progenitor pools as well the development of mature lymphoid and myeloid cells [Lyman, S, Jacobsen, S, *Blood*, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, PI3-kinase, Grb-2, SHIP and Src related kinases [Scheijen, B, Griffin J D, *Oncogene*, 2002, 21, 3314-3333]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype [Scheijen, B, Griffin J D, *Oncogene*, 2002, 21, 3314-3333].

c-fms encodes for macrophage colony stimulating factor receptor (M-CSF-1R) which is expressed predominately in the monocytes/macrophage lineage [Dai, X M et al., *Blood*, 2002, 99, 111-120]. MCSF-1R and its ligand regulate macrophage lineage growth and differentiation. Like the other family members, MCSF-1R contains an intrinsic kinase domain that is activated upon ligand-induced dimerization of the receptor. MCSF-1R is also expressed in non-hematopoietic cells including mammary gland epithelial cells and neurons. Mutations in this receptor are potentially linked to myeloid leukemias and its expression is correlated with metastatic breast, ovarian and endometrial carcinomas [Reilly, J T, *British Journal of Haematology*, 2002, 116, 744-757 and Kacinski, B M, *Mol. Reprod. and Devel.*, 1997, 46, 71-74]. Another possible indication for antagonists of MCSF-1R is osteoporosis [Teitelbaum, S, *Science* 2000, 289, 1504-1508.

PDGF-receptor (PDGFR) has two subunits-PDGFR-α and PDGFR-β, which can form homo or heterodimers upon ligand binding. There are several PDGF ligands: AB, BB, CC and DD. PDGFR is expressed on early stem cells, mast cells, myeloid cells, mesenchymal cells and smooth muscle cells [Scheijen, B, Griffin J D, *Oncogene*, 2002, 21, 3314-3333]. Only PDGFR-β has been implicated in myeloid leukemias—usually as a translocation partner with Tel, Huntingtin interacting protein (HIP1) or Rabaptin5. Recently it was shown that activation mutations in PDGFR-α kinase domain are in gastrointestinal stromal tumors (GIST) [Heinrich, M C et al., *Sciencexpress,* 2003]

Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates* 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews* 2001, 2, 21-32; Flatt, P., Pietenpol, J., *Drug Metabolism Reviews* 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the over-expression of cyclin D1 is commonly associated with numerous human cancers including breast, colon, hepatocellular carcinomas and gliomas [Flatt, P., Pietenpol, J., *Drug Metabolism Reviews* 2000, 32, 283-305]. The CDK2/cyclin E complex plays a key role in the progression from the early G1 to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal* 2000, 6, 192-212].

CDKs, especially CDK2, also play a role in apoptosis and T-cell development. CDK2 has been identified as a key regulator of thymocyte apoptosis [Williams, O., et al, *European Journal of Immunology* 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates* 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates*, 2000 3, 83-88].

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia*, 1993, 7, 1416. Furthermore, antisense Src expressed in ovarian and colon tumor cells has been shown to inhibit tumor growth. Wiener et al., *Clin. Cancer Res.*, 1999, 5, 2164; Staley et al., *Cell Growth Diff.*, 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature*, 1992, 357, 161. Hck, Fgr and Lyn have been identified as important mediators of integrin signaling in myeloid leukocytes. Lowell et al., *J. Leukoc. Biol.*, 1999, 65, 313. Inhibition of these kinase mediators may therefore be useful for treating inflammation. Boschelli et al., *Drugs of the Future* 2000, 25(7), 717.

Syk is a tyrosine kinase that plays a critical role in FcεRI mediated mast cell degranulation and eosiniphil activation. Accordingly, Syk kinase is implicated in various allergic disorders, in particular asthma. It has been shown that Syk binds to the phosphorylated gamma chain of the FcεRI receptor via N-terminal SH2 domains and is essential for downstream signaling [Taylor et al, *Mol. Cell. Biol.* 1995, 15, 4149].

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense) [Yousefi et al, *J Exp Med* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al, *Mol Cell Biol* 1998, 18, 4209]. It has also been reported that aerosolized Syk antisense suppresses Syk expression and mediator release from macrophages [Stenton et al, *J Immunology* 2000, 164, 3790].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [*Frank Mol. Med.* 5, 432-456 (1999) & Seidel, et al, *Oncogene* 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, *Blood* 96, 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, *Nature* 346, 274-276 (1990) & Galli, *N. Engl. J. Med.*, 328, 257-265 (1993)]. A crucial role for JAK3 in IgE receptor-mediated mast cell responses in vitro and in vivo has been established [Malaviya, et al, *Biochem. Biophys. Res. Commun.* 257, 807-813 (1999)]. In addition, the prevention of type I hypersensitivity reactions, including anaphylaxis, mediated by mast cell-activation through inhibition of JAK3 has also been reported [Malaviya et al, *J. Biol. Chem.* 274, 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 33, 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus Kinases (JAK 1 & 3) and that IL-4-associated JAK kinases are expressed in the RA synovium [Muller-Ladner, et al, *J. Immunol.* 164, 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, *Biochem. Biophys. Res. Commun.* 267, 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, *Clin. Cancer Res.* 5, 1569-1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, *EMBO J.* 17, 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, *Proc. Nat. Acad. Sci. U.S.A.* 94, 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, *J. Immunol.* 159, 5206-5210 (1997)]. In addition, IL-6-mediated STAT3 activation was blocked by an inhibitor of JAK, leading to sensitization of myeloma cells to apoptosis [Catlett-Falcone, et al, *Immunity* 10, 105-115 (1999)].

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature,* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell. Biol.* 1996, 16, 5313-5327; Amano et al., *Science,* 1997, 275, 1308-1311; Ishizaki et al., *FEBS Lett.* 1997, 404, 118-124) and in down-regulation of myosin phosphatase (Kimura et al., *Science,* 1996, 273, 245-248), platelet activation (Klages et al., *J. Cell. Biol.,* 1999, 144, 745-754), aortic smooth muscle contraction by various stimuli (Fu et al., *FEBS Lett.,* 1998, 440, 183-187), thrombin-induced responses of aortic smooth muscle cells (Seasholtz et al., *Cir. Res.,* 1999, 84, 1186-1193), hypertrophy of cardiomyocytes (Kuwahara et al., *FEBS Lett.,* 1999, 452, 314-318), bronchial smooth muscle contraction (Yoshii et al., *Am. J. Respir. Cell Mol. Biol.,* 1999, 20, 1190-1200), smooth muscle contraction and cytoskeletal reorganization of non-muscle cells (Fukata et al., *Trends in Pharm. Sci* 2001, 22, 32-39), activation of volume-regulated anion channels (Nilius et al., *J. Physiol.,* 1999, 516, 67-74), neurite retraction (Hirose et al., *J. Cell. Biol.,* 1998, 141, 1625-1636), neutrophil chemotaxis (Niggli, *FEBS Lett.,* 1999, 445, 69-72), wound healing (Nobes and Hall, *J. Cell. Biol.,* 1999, 144, 1235-1244), tumor invasion (Itoh et al., *Nat. Med.,* 1999, 5, 221-225) and cell transformation (Sahai et al., *Curr. Biol.,* 1999, 9, 136-145). More specifically, ROCK has been implicated in various diseases and disorders including hypertension (Satoh et al., *J. Clin. Invest.* 1994, 94, 1397-1403; Mukai et al., *FASEB J.* 2001, 15, 1062-1064; Uehata et al., *Nature* 1997, 389, 990-994; Masumoto et al., *Hypertension,* 2001, 38, 1307-1310), cerebral vasospasm (Sato et al., *Circ. Res.* 2000, 87, 195-200; Miyagi et al., *J. Neurosurg.* 2000, 93, 471-476; Tachibana et al., *Acta Neurochir (Wien)* 1999, 141, 13-19), coronary vasospasm (Shimokawa et al., *Jpn. Cir. J.* 2000, 64, 1-12; Kandabashi et al., *Circulation* 2000, 101, 1319-1323; Katsumata et al., *Circulation* 1997, 96, 4357-4363; Shimokawa et al., *Cardiovasc. Res.* 2001, 51, 169-177; Utsunomiya et al., *J. Pharmacol.* 2001, 134, 1724-1730; Masumoto et al., *Circulation* 2002, 105, 1545-1547), bronchial asthma (Chiba et al., *Comp. Biochem. Physiol. C Pharmacol. Toxicol. Endocrinol.* 1995, 11, 351-357; Chiba et al., *Br. J. Pharmacol.* 1999, 127, 597-600; Chiba et al., *Br. J. Pharmacol.* 2001, 133, 886-890; Iizuka et al., *Eur. J. Pharmacol.* 2000, 406, 273-279), preterm labor (Niro et al., *Biochem. Biophys. Res. Commun.* 1997, 230, 356-359; Tahara et al., *Endocrinology* 2002, 143, 920-929; Kupittayanant et al., *Pflugers Arch.* 2001, 443, 112-114), erectile dysfunction (Chitaley et al., *Nat. Med.* 2001, 7, 119-122; Mills et al., *J. Appl. Physiol.* 2001, 91, 1269-1273), glaucoma (Honjo et al., *Arch. Opthalmol.* 2001, 1171-1178; Rao et al., *Invest. Opthalmol. Vis. Sci.* 2001, 42, 1029-1037), vascular smooth muscle cell proliferation (Shimokawa et al., *Cardiovasc. Res.* 2001, 51, 169-177; Morishige et al., *Arterioscler. Thromb. Vasc. Biol.* 2001, 21, 548-554; Eto et al., *Am. J. Physiol. Heart Circ. Physiol.* 2000, 278, H1744-H1750; Sawada et al., *Circulation* 2000, 101, 2030-2023; Shibata et al., *Circulation* 2001, 103, 284-289), myocardial hypertrophy (Hoshijima et al., *J. Biol. Chem.* 1998, 273, 7725-77230; Sah et al., *J. Biol. Chem.* 1996, 271, 31185-31190; Kuwahara et al., *FEBS Lett.* 1999, 452, 314-318; Yanazume et al., *J. Biol. Chem.* 2002, 277, 8618-8625), malignoma (Itoh et al., *Nat. Med.* 1999, 5, 221-225; Genda et al., *Hepatology* 1999, 30, 1027-1036; Somlyo et al., *Biochem. Biophys. Res. Commun.* 2000, 269, 652-659), ischemia/reperfusion-induced injury (Ikeda et al., *J. of Surgical Res.* 2003, 109, 155-160; Miznuma et al. *Transplantation* 2003, 75, 579-586), endothelial dysfunction (Hernandez-Perera et al., *Circ. Res.* 2000, 87, 616-622; Laufs et al., *J. Biol. Chem.* 1998, 273, 24266-24271; Eto et al., *Circ. Res.* 2001, 89, 583-590), Crohn's Disease and colitis (Segain et al. *Gastroenterology* 2003, 124(5), 1180-1187), neurite outgrowth (Fournier et al. *J. Neurosci.* 2003, 23, 1416-1423), Raynaud's Disease (Shimokawa et al. *J. Cardiovasc. Pharmacol.* 2002, 39, 319-327), and atherosclerosis (Retzer et al. *FEBS Lett.* 2000, 466, 70-74; Ishibashi et al. *Biochim. Biophys. Acta* 2002, 1590, 123-130). Accordingly, the development of inhibitors of ROCK kinase would be useful as therapeutic agents for the treatment of disorders implicated in the ROCK kinase pathway.

ERK2 (extracellular signal regulated kinase) is a member of the mammalian mitogen-activated protein (MAP)1 kinase family. (MAP)1 kinases are serine/threonine kinases that mediate intracellular signal transduction pathways (Cobb and Goldsmith, *J. Biol. Chem.*, 1995, 270, 14843; Davis, *Mol. Reprod. Dev.* 1995, 42, 459) and are activated by mitogens and growth factors (Bokemeyer et al. *Kidney Int.* 1996, 49, 1187). Members of the MAP kinase family share sequence similarity and conserved structural domains, and, in addition to ERK2, include the JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., *Cell* 1994, 76, 1025; Han et al., *Science* 1994, 265, 808; Raingeaud et al., *J. Biol. Chem.* 1995, 270, 7420; Shapiro and Dinarello, *Proc. Natl. Acad. Sci. USA* 1995, 92, 12230). In contrast, ERKs are activated by mitogens and growth factors (Bokemeyer et al., *Kidney Int.* 1996, 49, 1187).

ERK2 is a widely distributed protein kinase that achieves maximum activity when both Thr183 and Tyr185 are phosphorylated by the upstream MAP kinase kinase, MEK1 (Anderson et al., *Nature* 1990, 343, 651; Crews et al., *Science* 1992, 258, 478). Upon activation, ERK2 phosphorylates many regulatory proteins, including the protein kinases Rsk90 (Bjorbaek et al., *J. Biol. Chem.* 1995, 270, 18848) and MAPKAP2 (Rouse et al., *Cell* 1994, 78, 1027), and transcription factors such as ATF2 (Raingeaud et al., *Mol. Cell. Biol.* 1996, 16, 1247), Elk-1 (Raingeaud et al., *Mol. Cell. Biol.* 1996, 16, 1247), c-Fos (Chen et al., *Proc. Natl. Acad. Sci. USA* 1993, 90, 10952), and c-Myc (Oliver et al., *Proc. Soc. Exp. Biol. Med.* 1995, 210, 162). ERK2 is also a downstream target of the Ras/Raf dependent pathways (Moodie et al., *Science* 1993, 260, 1658) and may help relay the signals from these potentially oncogenic proteins. ERK2 has been shown to play a role in the negative growth control of breast cancer cells (Frey and Mulder, *Cancer Res.* 1993, 57, 628) and hyperexpression of ERK2 in human breast cancer has been reported (Sivaraman et al., *J. Clin. Invest.* 1997, 99, 1478). Activated ERK2 has also been implicated in the proliferation of endothelin-stimulated airway smooth muscle cells, suggesting a role for this kinase in asthma (Whelchel et al., *Am. J. Respir. Cell Mol. Biol.* 1997, 16, 589).

Glycogen synthase kinase-3 (GSK-3) is a serine/threonine protein kinase comprised of α and β isoforms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., Neuron, 2003, 38, 547-554), and thus other β-amyloid-lowering strategies (e.g., the development of agents capable of inhibiting β-amyloid peptide) would be useful in the treatment of Alzherimer's disease and other psychotic and neurodegenerative disorders. Additionally, the neurofibrillary tangles contain hyperphosphorylated Tau protein, in which Tau is phosphorylated on abnormal sites, and thus agents capble of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., Current Biology 1994, 4, 1077-86; and Brownlees et al., Neuroreport 1997, 8, 3251-55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of Aβ peptides through the inhibition of GSK-3 (Phiel et al. Nature 2003, 423, 435-439). Thus, the development of inhibitors of GSK-3 would be useful for the reduction of the formation of amyloid plaques and neurofibrillry tangles, the pathological hallmarks of Alzheimer's Disease, and would also be useful for the treatment of other psychotic and neurodegenerative disorders.

Another substrate of GSK-3 is O-catenin, which is degradated after phosphorylation by GSK-3. Reduced levels of β-catenin have been reported in schizophrenic patients and have also been associated with other diseases related to increase in neuronal cell death [Zhong et al., Nature 1998, 395, 698-702; Takashima et al., PNAS 1993, 90, 7789-93; and Pei et al., J. Neuropathol. Exp 1997, 56, 70-78].

GSK-3 activity is also associated with stroke [Wang et al., Brain Res 2000, 859, 381-5; Sasaki et al., Neurol Res 2001, 23, 588-92; Hashimoto et al., J. Biol. Chem. 2002, 277, 32985-32991].

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., Curr. Biol. 1999, 9, R521). This sub-family includes PKA, PKB (c-Akt), PKC, PRK1, 2, $p70^{S6K}$, and PDK.

AKT (also known as PKB or Rac-PK beta), a serine/threonine protein kinase, has been shown to be overexpressed in several types of cancer and is a mediator of normal cell functions [(Khwaja, A., Nature 1999, 401, 33-34); (Yuan, Z. Q., et al., Oncogene 2000, 19, 2324-2330); (Namikawa, K., et al., J. Neurosci. 2000, 20, 2875-2886,)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., Proc. Natl. Acad. Sci. USA 1992, 89, 9267-9271); (Brodbeck, D. et al., J. Biol. Chem. 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., Mol. Cell. Biol., 1997, 17, 1595-1606,); (Hemmings, B. A., Science, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., J. Biol. Chem. 1998, 273, 7201-7204) induction of differentiation and/or proliferation, protein synthesis and stress responses (Alessi, D. R. et al., Curr. Opin. Genet. Dev. 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., Proc. Natl. Acad. Sci. U.S.A. 1992, 89, 9267-9271). It has also been found to be overexpressed in 12% of pancreatic cancers (Cheng, J. Q. et al., Proc. Natl. Acad. Sci. U.S.A. 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., Int. J. Cancer 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., Semin. Cancer Biol. 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., Recent Prog. Horm. Res. 1988, 44, pp. 307). Three isoforms of the catalytic subunit (C-α, C-β and C-γ) have been reported to date (Beebe, S. J. et al., J. Biol. Chem. 1992, 267, 25505-25512) with the C-α subunit being the most extensively studied, primarily because of its elevated expression in primary and metastatic melanomas (Becker, D. et al., Oncogene 1990, 5, 1133). To date, strategies to modulate the activity of the C-α subunit involve the use of antibodies, molecules that block PKA activity by targeting regulatory dimers and antisense oligonucleotides expression.

The ribosomal protein kinases $p70^{S6K}$-1 and -2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., Prog. Nucleic Acid Res. Mol. Biol. 2001, 65, 101-186). $p70^{S6K}$ dependent S6 phosphorylation is stimulated in response to a variety of hormones and growth factors primarily via the PI3K pathway (Coffer, P. J. et al., Biochem. Biophys. Res.

Commun, 1994 198, 780-786), which may be under the regulation of mTOR, since rapamycin acts to inhibit p70$^{S6K}$ activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.*, 1998, 8, 69-81). The use of rapamycin and gene deletion studies of dp70S6K from *Drosophila* and p70$^{S6K}$1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.*, 1997 57, 5221-5225), (Brognard, J. et al., *Cancer Res.*, 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer. Ther.* 2002, 1, 707), colon [(*Neoplasia* 2001, 3, 278), (Arico, S. et al., *J. Biol. Chem.* 2002, 277, 27613-27621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biol.* 2000, 10, 1439-1442)].

Accordingly, there is a great need to develop inhibitors of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK protein kinases that are useful in treating various diseases or conditions associated with FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK activation, particularly given the inadequate treatments currently available for the majority of these disorders.

SUMMARY OF THE INVENTION

It has now been found that compounds of this invention, and pharmaceutically acceptable compositions thereof, are effective as inhibitors of kinases. In certain embodiments, these compounds are effective as inhibitors of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK protein kinases. In other embodiments, these compounds are effective as inhibitors of FLT-3 and/or c-KIT protein kinases. These compounds have the general formula A:

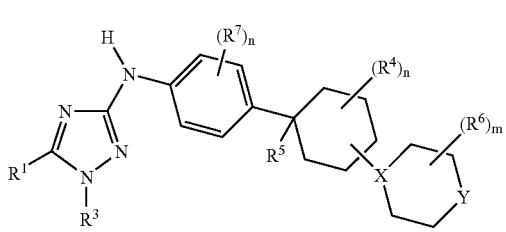

wherein $R^1$, $R^3$, $R^4$, $R^5$, $R^6$, and $R^7$ are as described below.

These compounds and pharmaceutical compositions thereof are useful for treating or preventing a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

DETAILED DESCRIPTION OF THE INVENTION

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined herein below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —P(O)$_2$R°; —PO(R°)$_2$; —OPO(R°)$_2$; —(CH$_2$)$_{0-2}$NHC(O)R°; phenyl (Ph) optionally substituted with R°; —O(Ph) optionally substituted with R°; —(CH$_2$)$_{1-2}$(Ph), optionally substituted with R°; or —CH=CH(Ph), optionally substituted with R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or halo C$_{1-4}$aliphatic, wherein each of the foregoing C$_{1-4}$aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

In the case of a heterocyclyl substitutions, substituents can be attached to substitutable positions both at the carbon atom and at the heteroatom. For example, if the described substituted structure were a piperazine ring and the substituent were CH$_3$, the described compound could either be

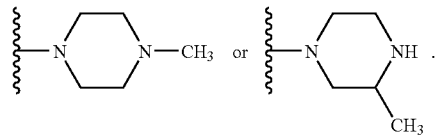

In one embodiment, the present invention relates to a compound of formula I:

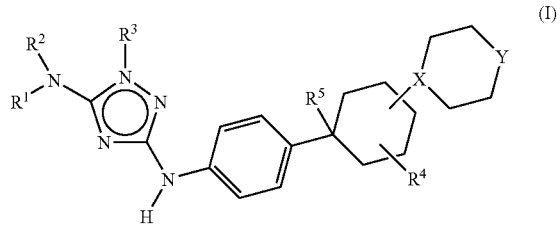

wherein

X is CH or N;

Y is CH$_2$, NH, NR, O, or S;

R$^1$ is hydrogen or C$_{1-6}$alkyl;

R$^2$ is hydrogen;

R$^3$ is an optionally substituted aryl group selected from a 5-6 membered monocyclic or an 8-12 membered bicyclic ring; said aryl group having 0-3 heteroatoms independently selected from nitrogen, oxygen, or sulfur;

R$^5$ is hydrogen, —C$_{1-6}$aliphatic, —CN, —OH, —O(C$_{1-6}$aliphatic), —CO$_2$H, —CO$_2$(C$_{1-6}$aliphatic), —CON(R)$_2$, —O(haloC$_{1-4}$ aliphatic), -haloC$_{1-4}$aliphatic, —NO$_2$, -halogen, —NR$^{12}$, or —C$_{1-6}$aliphatic optionally substituted with NH$_2$;

R$^4$ is hydrogen, halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C(S)R°; —NR°C(O)N(R°)$_2$;

—NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —C(=NH)—N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; —(CH₂)₀₋₂NHC(O)R°, =O, =S, =NNHR*, =NN(R*)₂, =NNHC(O)R*, =NNHCO₂(alkyl), =NNHSO₂(alkyl), or =NR*, wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH₂(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

an aliphatic group of R° is optionally substituted with NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of these foregoing $C_{1-4}$ aliphatic groups is unsubstituted;

each R* is independently selected from hydrogen or a $C_{1-6}$ aliphatic optionally substituted with NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of these foregoing $C_{1-4}$ aliphatic groups is unsubstituted; and R is hydrogen or a $C_{1-6}$ aliphatic group, optionally substituted with =O, =S, —NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of these foregoing $C_{1-4}$ aliphatic groups is unsubstituted.

Another embodiment of the invention relates to a compound of formula II:

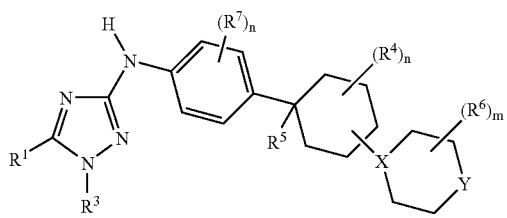

(II)

wherein

X is CH or N;

Y is CH₂, NH, NR, O, or S;

n is 0-4;

m is 0-4;

$R^1$ is hydrogen or —N(H)$R^2$;

$R^2$ is hydrogen or $C_{1-6}$ aliphatic;

$R^3$ is an aryl group selected from a 5-6 membered monocyclic or an 8-12 membered bicyclic ring; said aryl group having 0-3 heteroatoms independently selected from nitrogen, oxygen, or sulfur wherein each substitutable position of $R^3$ is optionally and independently replaced by $R^7$;

$R^5$ is hydrogen, —$C_{1-6}$aliphatic, —CN, —OH, —O($C_{1-6}$aliphatic), —CO₂H, —CO₂($C_{1-6}$aliphatic), —CON(R°)₂, —NO₂, -halogen, —NR°₂, wherein each substitutable position of an aliphatic carbon is optionally and independently substituted with halogen or NH₂;

$R^7$ is halogen; —R°; —OR°; —SR°; 1,2-methylenedioxy; 1,2-ethylenedioxy; phenyl (Ph) optionally substituted with R°; —O(Ph) optionally substituted with R°; —(CH₂)$_{1-2}$(Ph), optionally substituted with R°; —CH=CH(Ph), optionally substituted with R°; —NO₂; —CN; —N(R°)₂; —NR°C(O)R°; —NR°C(S)R°; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; or —(CH₂)₀₋₂NHC(O)R°;

each $R^4$ and $R^6$ is hydrogen; halogen; —R°; —OR°; —SR°; 1,2-methylenedioxy; 1,2-ethylenedioxy; phenyl (Ph) optionally substituted with R°; —O(Ph) optionally substituted with R°; —(CH₂)$_{1-2}$(Ph) optionally substituted with R°; —CH=CH(Ph) optionally substituted with R°; —NO₂; —CN; —N(R°)₂; —NR°C(O)R°; —NR°C(S)R°; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —C(=NH)—N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; —(CH₂)₀₋₂NHC(O)R°, =O, =S, =NNHR*, =NN(R*)₂, =NNHC(O)R*, =NNHCO₂(alkyl), =NNHSO₂(alkyl), or =NR*.

X and Y and the atoms to which they are attached form a six membered ring, preferably with 2 heteroatoms, and more preferably with 1 heteroatom.

$R^4$, $R^6$, and $R^7$ are attached at any substitutable positions around the rings as shown in formula II. In the case of a heterocyclyl substitution, $R^4$, $R^6$, and $R^7$ can be attached to substitutable positions both at the carbon atom and at the heteroatom. For example, if X and Y were both N and $R^6$ were CH₃, the third monocycle of formula II could be either

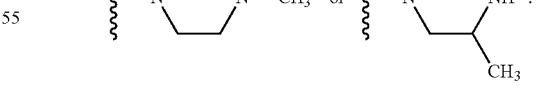

In another embodiment of the invention, there is provided a compound of formula (II) wherein X is CH or N;

Y is CH₂, NH, NR°, O, or S;

n is 0-4;

m is 0-4;

$R^1$ is hydrogen or —N(H)R $R^2$ is hydrogen or $C_{1-6}$ alkyl;

$R^3$ is an aryl group selected from a 5-6 membered monocyclic or an 8-12 membered bicyclic ring; said aryl group having 0-3 heteroatoms independently selected from nitrogen, oxygen, or sulfur wherein each substitutable position of $R^3$ is optionally and independently replaced by $R^7$;

$R^5$ is hydrogen, —$C_{1-6}$aliphatic, —CN, —OH, —O($C_{1-6}$aliphatic), —$CO_2H$, —$CO_2(C_{1-6}$aliphatic), —CON($R^o$)$_2$, -halogen, or —$NR^{12}$, wherein each substitutable position of an aliphatic carbon is optionally and independently substituted with halogen;

$R^7$ is halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —N($R^o$)$_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(S)$R^o$; —C(O)N($R^o$)$_2$; —C(S)N($R^o$)$_2$; —OC(O)N($R^o$)$_2$; —OC(O)$R^o$; —C(O)N(O$R^o$)$R^o$; —C(NO$R^o$)$R^o$; —S(O)$_2R^o$; —S(O)$_3R^o$; —$SO_2$N($R^o$)$_2$; —S(O)$R^o$; —$NR^oSO_2N(R^o)_2$; —$NR^oSO_2R^o$; —N(O$R^o$)$R^o$; —C(=NH)—N($R^o$)$_2$; or —$(CH_2)_{0-2}$NHC(O)$R^o$ wherein each independent occurrence of $R^o$ is selected from hydrogen, optionally substituted $C_{1-6}$ aliphatic, an unsubstituted 5-6 membered heteroaryl or heterocyclic ring (provided that a nitrogen atom in the heterocyclic ring is optionally substituted with —$R^+$ or —C(O)$R^+$, wherein $R^+$ is ($C_{1-6}$alkyl), preferably ($C_{1-4}$alkyl)), phenyl, —O(Ph), or —$CH_2$(Ph), or, notwithstanding the definition above, two independent occurrences of $R^o$, on the same substituent or different substituents, taken together with the atom(s) to which each $R^o$ group is bound, form a 5-8-membered heterocyclyl, aryl, or heteroaryl ring or a 3-8-membered cycloalkyl ring having 0-3 heteroatoms independently selected from nitrogen, oxygen, or sulfur.

Each $R^4$ and $R^6$ is independently halogen; —$R^o$; —$OR^o$; —$SR^o$; 1,2-methylenedioxy; 1,2-ethylenedioxy; phenyl (Ph) optionally substituted with $R^o$; —O(Ph) optionally substituted with $R^o$; —$(CH_2)_{1-2}$(Ph) optionally substituted with $R^o$; —CH=CH(Ph) optionally substituted with $R^o$; —CN; —N($R^o$)$_2$; —$NR^oC(O)R^o$; —$NR^oCO_2R^o$; —C(O)$CH_2$C(O)$R^o$; —$CO_2R^o$; —C(O)$R^o$; —C(O)N($R^o$)$_2$; —OC(O)N($R^o$)$_2$; —OC(O)$R^o$; —S(O)$_2R^o$; —$SO_2$N($R^o$)$_2$; —S(O)$R^o$; —$NR^oSO_2R^o$; or =O;

An aliphatic group of $R^o$ is optionally substituted with $NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2(C_{1-4}$ aliphatic), wherein each of these foregoing $C_{1-4}$ aliphatic groups is optionally substituted with halogen;

R is hydrogen or a $C_{1-6}$ aliphatic group, optionally substituted with =O, =S, —$NH_2$, NH($C_{1-4}$ aliphatic), N($C_{1-4}$ aliphatic)$_2$, halogen, $C_{1-4}$ aliphatic, OH, O($C_{1-4}$ aliphatic), $NO_2$, CN, $CO_2H$, $CO_2(C_{1-4}$ aliphatic), wherein each of these foregoing $C_{1-4}$aliphatic groups is optionally substituted with halogen.

According to one embodiment of formula I, $R^1$ is hydrogen.

According to one embodiment of formulae II, $R^1$ is hydrogen. In another embodiment of formula II, $R^1$ is N(H)$R^2$.

According to another embodiment of either of formula I or II, $R^2$ is hydrogen.

According to another embodiment of either of formula I or II, if X is CH, then Y is not $CH_2$.

According to another embodiment of either of formula I or II, X is N.

According to another embodiment of either of formula I or II, Y is O.

According to another embodiment of either of formula I or II, Y is NR.

In some embodiments of formula II, m, n and p and are each independently 1 or 2. In another embodiment, m is 0; in another embodiment m is 1. In one embodiment n is 0; in another embodiment n is 1. In another embodiment, p is 0; in another embodiment, p is 1. In a further embodiment, each of m, n and p are 0.

In some embodiments of formula II, $R^4$, $R^6$, and $R^7$ are each independently halogen; $C_{1-4}$ aliphatic; —$OR^o$; phenyl (Ph) optionally substituted with $R^o$; —O(Ph) optionally substituted with $R^o$; —$(CH_2)_{1-2}$(Ph) optionally substituted with $R^o$; —CH=CH(Ph) optionally substituted with $R^o$; —CN; —N($R^o$)$_2$; —$NR^oC(O)R^o$; —$NR^oCO_2R^o$; —C(O)$CH_2$C(O)$R^o$; —$CO_2R^o$; —C(O)$R^o$; —C(O)N($R^o$)$_2$; —OC(O)N($R^o$)$_2$; —OC(O)$R^o$; —S(O)$_2R^o$; —$SO_2$N($R^o$)$_2$; —S(O)$R^o$; —$NR^oSO_2R^o$; or two hydrogen atoms bonded to the same carbon atom are replaced by =O.

In other embodiments $R^4$, $R^6$, and $R^7$ are each independently halogen; $C_{1-4}$ aliphatic optionally substituted with halogen; —$OR^o$; —CN; —N($R^o$)$_2$; —$NR^oC(O)R^o$; —$NR^oCO_2R^o$; or two hydrogen atoms bonded to the same carbon atom are replaced by =O.

In other embodiments, $R^4$ and $R^6$ are $C_{1-6}$ alkyl or halogen, preferably $C_{1-3}$ alkyl, F, or Cl.

In another embodiment, $R^7$ is halogen, —CN, $C_{1-6}$ alkyl, $C_{1-6}$ alkoxy, —N(R)$_2$, or $C_{1-4}$ haloalkyl.

In some embodiments of formulae I and II, $R^3$ is an aryl group selected from a 6-membered monocyclic having 0-3 heteroatoms independently selected from nitrogen, oxygen, and sulfur wherein each substitutable position of $R^3$ is optionally replaced by $R^7$.

According to one embodiment, $R^3$ is an aryl group selected from a 6 membered monocyclic having 0, 1, or 2 heteroatoms independently selected from nitrogen, oxygen, and sulfur wherein each substitutable position of $R^3$ is optionally replaced by $R^7$.

According to another embodiment, $R^3$ is a 6 membered heteroaryl with 1 or 2 nitrogen heteroatoms, preferably 1 nitrogen atom. According to yet another embodiment, $R^3$ is 2-pyridyl.

In one embodiment of formulae I or II, $R^5$ is hydrogen, halogen, OH, $NR^o$, CN, O—($C_{1-6}$ aliphatic), or $C_{1-6}$ alkyl optionally substituted with —$NR_2$.

In another embodiment, $R^5$ is $C_{1-6}$ alkyl optionally substituted with —N(R)$_2$.

In another embodiment, $R^5$ is —CN. In yet another embodiment, $R^5$ is hydrogen.

One embodiment is represented by Formula I-a.

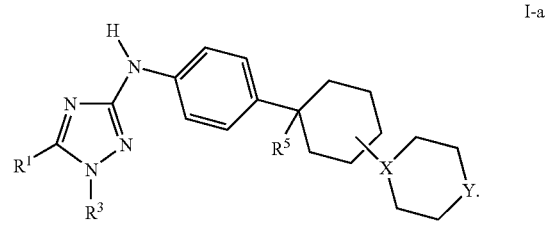

I-a

Another embodiment is represented by Formula I-b:

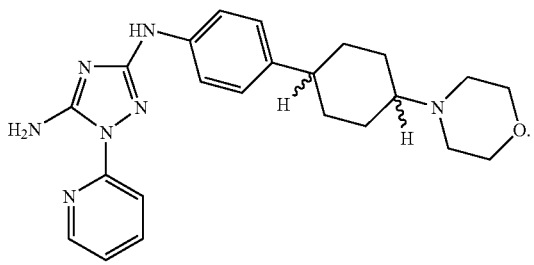

I-b

Another embodiment is represented by Formula I-c:

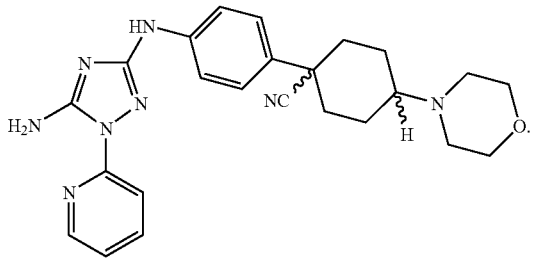

I-c

Other embodiments are represented by compounds I-1 and I-2:

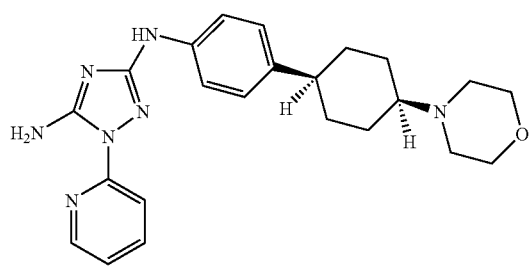

I-1

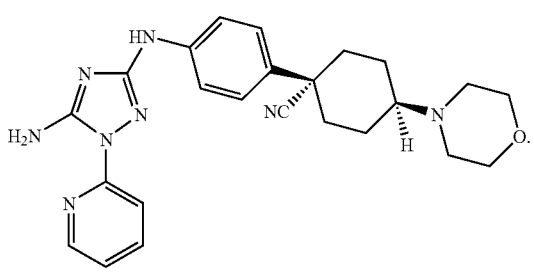

I-2

Other embodiments are represented by compounds I-3 and I-4:

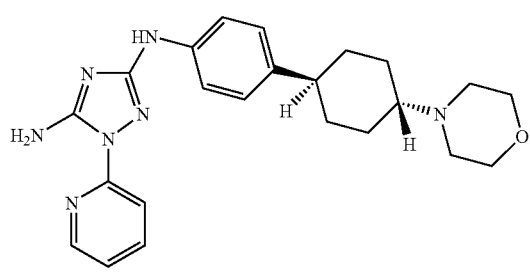

I-3

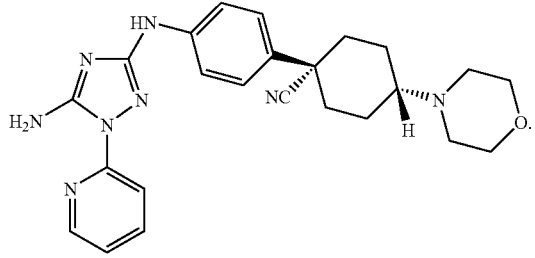

I-4

Compounds of this invention also include those wherein the ring containing X and Y is attached to the rest of the molecule at any atom, not just at the X atom.

In another embodiment, the invention provides a compound of formula (III)

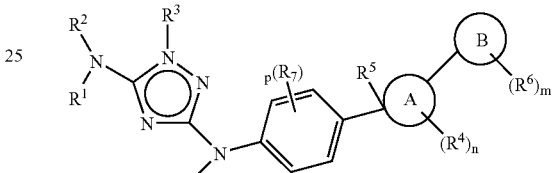

(III)

wherein

Ring A is a 3-8 membered saturated carbocyclic ring;

Ring B is a 3-8 membered saturated or partially saturated ring, wherein Ring B has 0-3 heteroatoms independently selected from nitrogen, oxygen, or sulfur;

X is CH or N;

Y is $CH_2$, NR, O, or S;

n is 0-4;

m is 0-4;

p is 0-4;

$R^1$ is hydrogen;

$R^2$ is hydrogen or $C_{1-6}$ aliphatic;

$R^3$ is an aryl group selected from a 5-6 membered monocyclic or an 8-12 membered bicyclic ring; said aryl group having 0-3 heteroatoms independently selected from nitrogen, oxygen, or sulfur wherein each substitutable position of $R^3$ is optionally and independently replaced by $R^7$;

$R^5$ is hydrogen, —$C_{1-6}$aliphatic, —CN, —OH, —O($C_{1-6}$aliphatic), —$CO_2H$, —$CO_2$($C_{1-6}$aliphatic), —CON(R—)$_2$, —$NO_2$, -halogen, —$NR^{12}$, wherein each substitutable position of an aliphatic carbon is optionally and independently replaced by halogen or $NH_2$;

$R^7$ is halogen; —R°; —OR°; —SR°; 1,2-methylenedioxy; 1,2-ethylenedioxy; phenyl (Ph) optionally substituted with R°; —O(Ph) optionally substituted with R°; —$(CH_2)_{1-2}$(Ph), optionally substituted with R°; —CH=CH(Ph), optionally substituted with R°; —$NO_2$; —CN; —N(R°)$_2$; —NR°C(O)R°; —NR°C(S)R°; —NR°C(O)N(R°)$_2$; —NR°C(S)N(R°)$_2$; —NR°$CO_2$R°; —NR°NR°C(O)R°; —NR°NR°C(O)N(R°)$_2$; —NR°NR°$CO_2$R°; —C(O)C(O)R°; —C(O)$CH_2$C(O)R°; —$CO_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —$S(O)_2$R°;

—S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°, wherein each independent occurrence of R° is selected from hydrogen, optionally substituted C$_{1-6}$ aliphatic, an unsubstituted 5-6 membered heteroaryl or heterocyclic ring (provided that a nitrogen atom in the heterocyclic ring is optionally substituted with —R$^+$ or —C(O)R$^+$, wherein R$^+$ is (C$_{1-6}$alkyl), preferably (C$_{1-4}$alkyl)), phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

each R$^4$ and R$^6$ is independently hydrogen; halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —C(=NH)—N(R°)$_2$, —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —(CH$_2$)$_{0-2}$NHC(O)R°, =O, =S, =NNHR*, =NN(R*)$_2$, =NNHC(O)R*, =NNHCO$_2$(alkyl), =NNHSO$_2$(alkyl), or =NR*, wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

an aliphatic group of R° is optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of these foregoing C$_{1-4}$ aliphatic groups is unsubstituted;

each R* is independently selected from hydrogen or a C$_{1-6}$ aliphatic optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of these foregoing C$_{1-4}$ aliphatic groups is unsubstituted; and R is hydrogen or a C$_{1-6}$ aliphatic group, optionally substituted with =O, =S, —NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of these foregoing Cl$_4$aliphatic groups is unsubstituted.

In a further embodiment, the invention provides a compound of formula III wherein R$^2$ is hydrogen or C$_{1-6}$ alkyl;

R$^5$ is hydrogen, —C$_{1-6}$aliphatic, —CN, —OH, —O(C$_{1-6}$aliphatic), —CO$_2$H, —CO$_2$(C$_{1-6}$aliphatic), —CON(R°)$_2$, -halogen, or —NR$^{12}$, wherein each substitutable position of an aliphatic carbon is optionally replaced by halogen;

each R$^4$, R$^6$, and R$^7$ is independently halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph) optionally substituted with R°; —CH=CH(Ph) optionally substituted with R°; —CN; —N(R°)$_2$; —NR°C(O)R°; —NR°CO$_2$R°; —C(O)CH$_2$C(O)R°; —CO$_2$R°; —C(O)R°; —C(O)N(R°)$_2$; —OC(O)N(R°)$_2$; —OC(O)R°; —S(O)$_2$R°; —SO$_2$N(R°)$_2$; —S(O)R°; or —NR°SO$_2$R°; or two hydrogen atoms bonded to the same carbon atom are replaced by =O;

wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur;

an aliphatic group of R° is optionally substituted with NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), wherein each of these foregoing C$_{1-4}$ aliphatic groups is optionally substituted with halogen; and R is hydrogen or a C$_{1-6}$ aliphatic group, optionally substituted with =O, =S, —NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), wherein each of these foregoing C$_{1-4}$aliphatic groups is optionally substituted with halogen.

According to a further embodiment of formula III, R$^2$ is hydrogen.

According to a further embodiment of formula III, any one or more of m, n and p are 0. According to a further embodiment, R$^4$, R$^6$, and R$^7$ are each independently halogen; C$_{1-4}$ aliphatic optionally substituted with halogen; —OR°; —CN; —N(R°)$_2$; —NR°C(O)R°; —NR°CO$_2$R°; or two hydrogen atoms bonded to the same carbon atom are replaced by =O. In yet a further embodiment, R$^4$ and R$^6$ are C$_{1-6}$ alkyl or halogen. In another embodiment, R$^7$ is halogen, —CN, C$_{1-6}$ alkyl, C$_{1-6}$ alkoxy, —N(R)$_2$, or C$_{1-4}$ haloalkyl.

In another embodiment of formula III, R$^3$ is an aryl group selected from a 6-membered monocyclic having 0-3 heteroatoms independently selected from nitrogen, oxygen, and sulfur wherein each substitutable position of R$^3$ is optionally replaced by R$^7$. In yet a further embodiment, R$^3$ is a 6 membered heteroaryl group having 1 or 2 nitrogen heteroatoms. In a still further embodiment, R$^3$ is 2-pyridyl.

According to a further embodiment of formula III, R$^5$ is hydrogen, halogen, OH, NR°, CN, O—(C$_{1-6}$ aliphatic), or C$_{1-6}$ alkyl optionally substituted with —NR$^2$. In a further embodiment, R$^5$ is C$_{1-6}$ alkyl optionally substituted with —N(R)$_2$. In yet a further embodiment, R$^5$ is —CN or hydrogen.

In another embodiment of formula III, Ring A is a 5-7 membered carbocyclic ring.

In another embodiment of formula III, Ring B is a 5-7 membered saturated or partially saturated ring. In a further embodiment, Ring B is a 5-7 membered saturated or partially saturated heterocyclic ring.

Other embodiments of formulae I, II and III are represented by the following compounds:
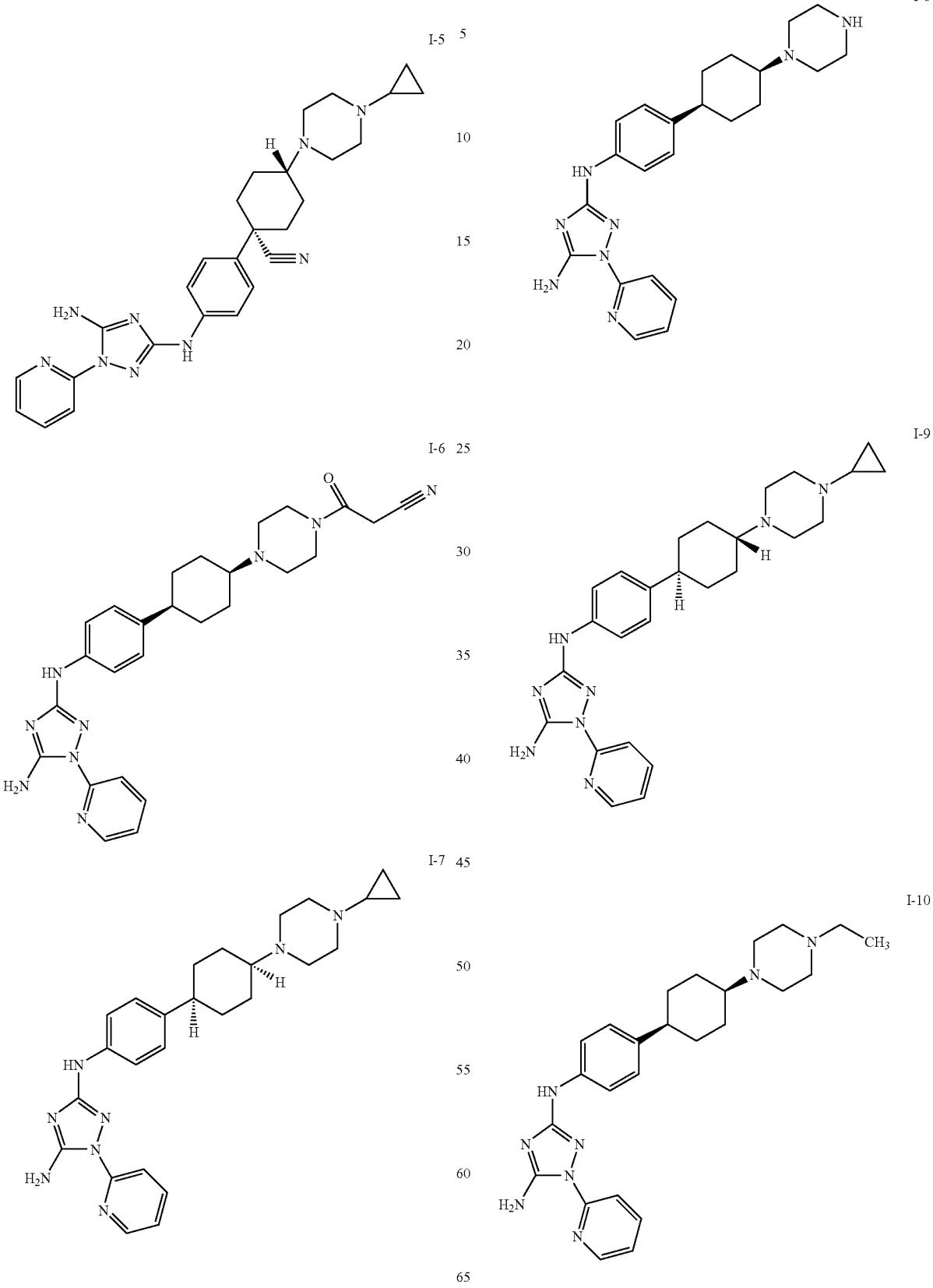

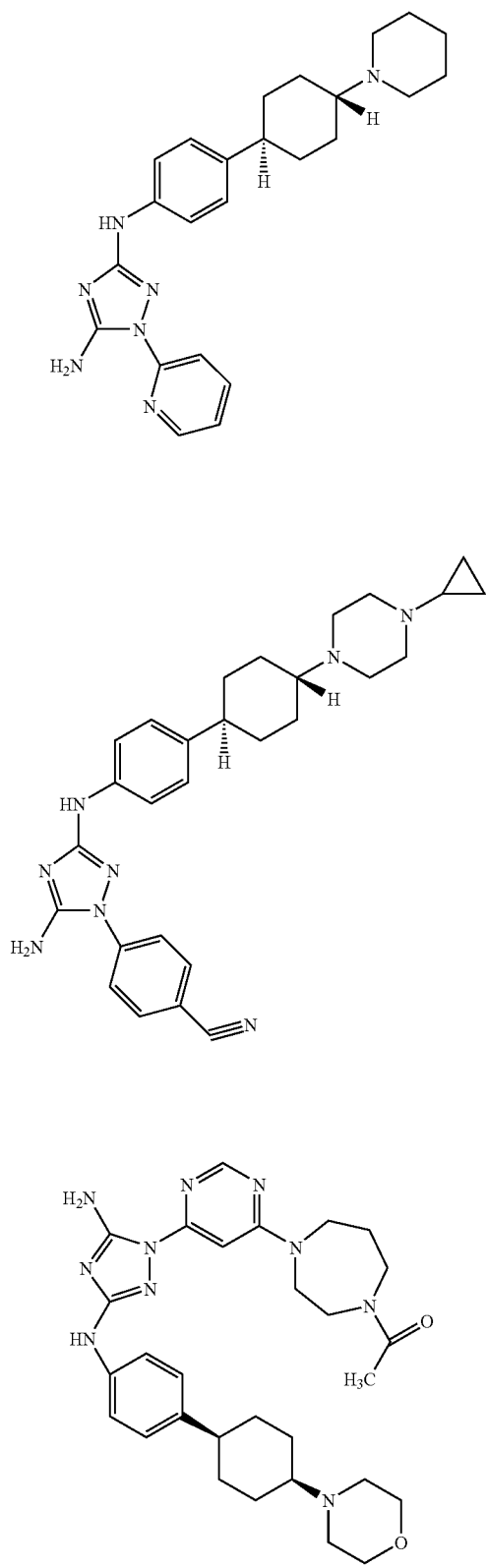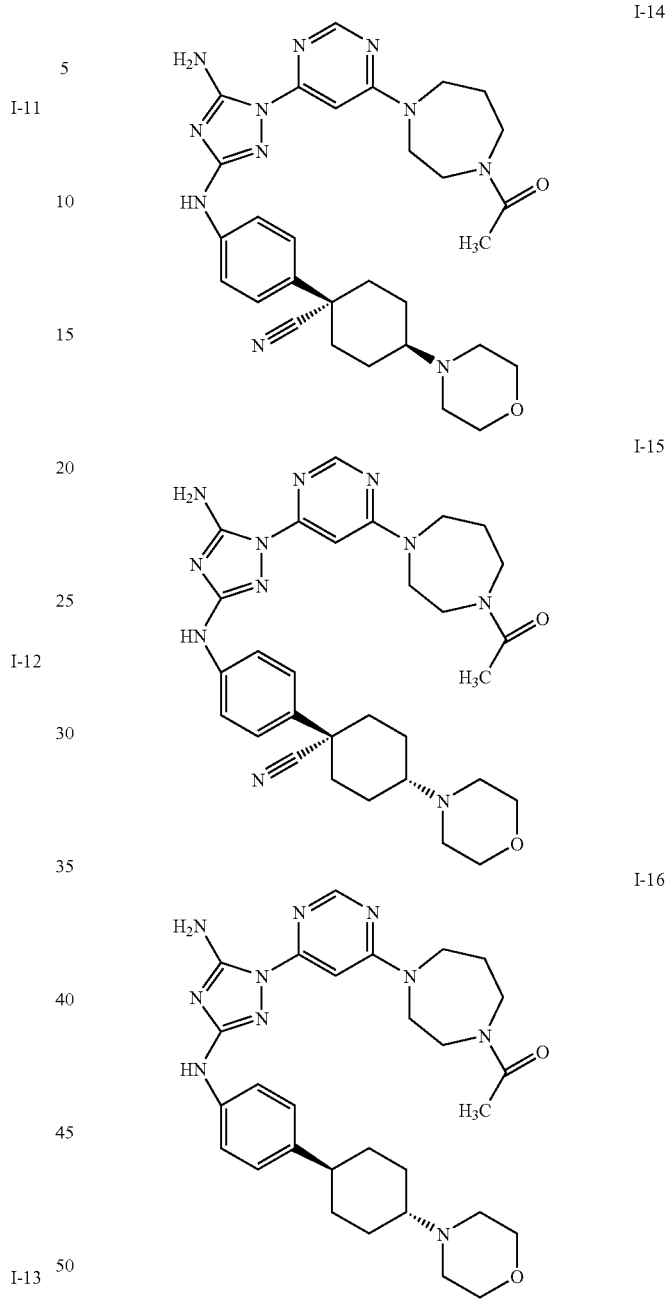

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK, and thus, without wishing to be bound by any particular theory, the compounds and compositions are particularly useful for treating or lessening the severity of a disease, condition, or disorder where activation of one or more of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK is implicated in the disease, condition, or disorder. When activation of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK is implicated in a particular disease, condition, or disorder, the disease, condition, or disorder may also be referred to as "FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK-mediated disease" or disease symptom. Accordingly, in another aspect, the present invention provides a method for treating or lessening the severity of a disease, condition, or disorder where activation or one or more of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK is implicated in the disease state.

The activity of a compound utilized in this invention as an inhibitor of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK, may be assayed in vitro, in vivo or in a cell line. In vitro assays include assays that determine inhibition of either the phosphorylation activity or ATPase activity of activated FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK. Alternate in vitro assays quantitate the ability of the inhibitor to bind to FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK. Inhibitor binding may be measured by radiolabelling the inhibitor prior to binding, isolating the inhibitor/FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, or SYK complex and determining the amount of radiolabel bound. Alternatively, inhibitor binding may be determined by running a competition experiment where new inhibitors are incubated with FLT-3, FMS, c-KIT, PDGFR, JAK, AGC sub-family of protein kinases (e.g., PKA, PDK, p70S6K–1 and -2, and PKB), CDK, GSK, SRC, ROCK, and/or SYK bound to known radioligands.

In one embodiment, the invention provides a compound of formulae I, II or III that selectively inhibits FLT-3 and/or c-KIT. In a further embodiment, the invention provides a compound of formula I that selectively inhibits FLT-3 and/or c-KIT. As used herein, the term "selectively inhibits" means that a compound inhibits FLT-3 and/or c-KIT with a K$_i$ or IC$_{50}$ that is at least two-fold lower than for one or more other kinases, such as Aurora-2, FMS, PDGFR, JAK, AGC sub-family of protein kinases (e.g., PKA, PDK, p70$^{S6K}$-1 and -2, and PKB), CDK, GSK-3, JNK, KDR, MET, SRC, ROCK and/or SYK. In a further embodiment, a compound that selectively inhibits FLT-3 and/or c-KIT is one that inhibits FLT-3 and/or c-KIT with a K$_i$ or IC$_{50}$ that is at least five-fold lower or at least ten-fold lower than for one or more other kinases, such as Aurora-2, FMS, PDGFR, JAK, AGC sub-family of protein kinases (e.g., PKA, PDK, p70$^{S6K}$-1 and -2, and PKB), CDK, GSK-3, JNK, KDR, MET, SRC, ROCK and/or SYK.

The term "measurably inhibit", as used herein means a measurable change in FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK activity between a sample comprising said composition and a FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK kinase and an equivalent sample comprising FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK kinase in the absence of said composition.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

According to another embodiment, the invention provides a method for treating or lessening the severity of a FMS-mediated disease or condition in a patient comprising the step of administering to said patient a composition according to the present invention.

The term "FMS-mediated disease", as used herein means any disease or other deleterious condition in which a FMS family kinase is known to play a role. Such conditions include, without limitation, cancer (including, but not limited to, ovarian, endometrial, and breast cancer), inflammatory disorders, and hypertension.

According to another embodiment, the invention provides a method for treating or lessening the severity of a c-KIT-mediated disease or condition in a patient comprising the step of administering to said patient a composition according to the present invention.

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma, colon carcinoma, and glioblastoma.

According to another embodiment, the invention provides a method for treating or lessening the severity of a CDK-2-mediated disease or condition in a patient comprising the step of administering to said patient a composition according to the present invention.

The term "CDK-2-mediated disease", as used herein means any disease or other deleterious condition in which CDK-2 is known to play a role. Accordingly, these compounds are useful for treating diseases or conditions that are known to be affected by the activity of CDK-2 kinase. Such diseases or conditions include cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, viral infections, neurodegenerative disorders, disorders associated with thymocyte apoptosis, or proliferative disorders resulting from the deregulation of the cell cycle, especially of the progression from $G_1$ to S phase.

According to another embodiment, the invention provides a method for treating or lessening the severity of a GSK-3-mediated disease or condition in a patient comprising the step of administering to said patient a composition according to the present invention.

According to another embodiment, the invention provides a method for treating or lessening the severity of a Src-mediated disease or condition in a patient comprising the step of administering to said patient a composition according to the present invention.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitus B infection.

According to another embodiment, the invention provides a method for treating or lessening the severity of a Syk-mediated disease or condition in a patient comprising the step of administering to said patient a composition according to the present invention.

The term "Syk-mediated disease" or "Syk-mediated condition", as used herein, means any disease or other deleterious condition in which Syk protein kinase is known to play a role. Such conditions include, without limitation, allergic disorders, especially asthma.

The term "JAK-mediated disease", as used herein means any disease or other deleterious condition in which a JAK family kinase is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer.

The term "$p70^{S6K}$-mediated condition" or "disease", as used herein, means any disease or other deleterious condition in which $p70^{S6K}$ is known to play a role. The term "p70S6K-mediated condition" or "disease" also means those diseases or conditions that are alleviated by treatment with a p70 inhibitor. $p70^{S6K}$ mediated diseases or conditions include, but are not limited to, proliferative disorders, such as cancer and tuberous sclerosis.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progessive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction.

In other embodiments, the invention relates to a method of enhancing glycogen synthesis and/or lowering blood levels of glucose in a patient in need thereof, comprising administering to said patient a therapeutically effective amount of a composition comprising a compound of formula I, II or III. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I, II or III. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I, II or III. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of cancer therapies see The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK activity in a biological sample or a patient, which method comprises administering to the patient, or contacting said biological sample with a compound of formula I, II or III or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK kinase activity in a biological sample is useful for a variety of purposes that are known to one of skill in the art. Examples of such purposes include, but are not limited to, blood transfusion, organ-transplantation, biological specimen storage, and biological assays.

EXAMPLES

Compounds of general formula I were prepared according to the general procedure as follows in Examples 1 and 2:

Example 1

N3-[4-(4-Morpholin-4-yl-cyclohexyl)-phenyl]-1-pyridin-2-yl-1H-[1,2,4]triazole-3,5-diamine

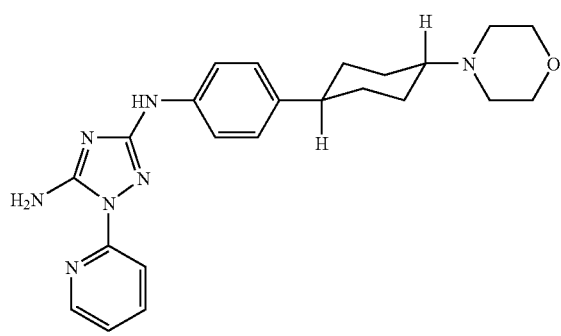

HPLC method A:

Clm: Lighting 3 um, 2.1×50 mm

Gradient: 100% B (0.1% TFA/1.0% MeCN/water) to 100% D (0.1% TFA/MeCN) over 4 min. Hold @100% D to 5.6 min, G0 to 100% B over 0.4 min, hold for 1 min.

Flow rate: 0.8 mL/min

Synthesis of dimethyl 4-cyano-4-(4-nitrophenyl)heptanedioate (2)

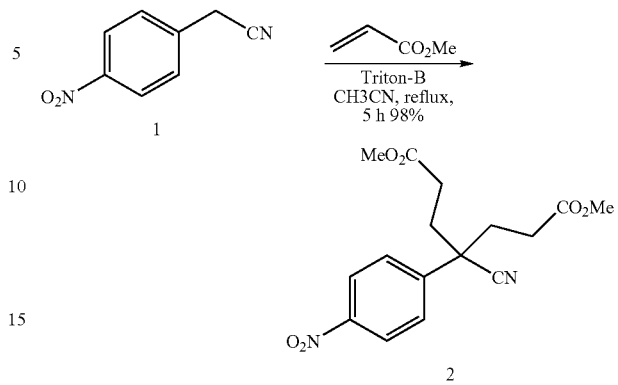

To a solution of 2-(4-nitrophenyl)acetonitrile (1) (50.12 g, 0.31 mol) in $CH_3CN$ (1 L) at RT under $N_2$ was added Triton-B/40% MeOH (14.5 mL, 0.03 mol) to give a dark purple solution. The mixture was heated to reflux then (over ~2.5 h) methyl acrylate (160 mL, 1.78 mol) was added and reflux continued for 4 h. The reaction was cooled and evaporated, then diluted with EtOAc and acidified with 2N HCl. The layers were separated, the aqueous was back extracted with EtOAc, the combined organics were washed with saturated NaCl solution, dried over $Na_2SO_4$, filtered and evaporated. Purification by flash chromatography on silica gel (1 L), eluted with 1:2 EtOAc:hexanes provided 2 as a yellow oil (88.96 g, 86%).

$^1$H-NMR (500 MHz, dmso-$d_6$) 8.31 (d, 2H), 7.78 (d, 2H), 3.52 (s, 6H), 2.4 (m, 6H), 2.05 (m, 2H) ppm.

MS-FIA: 333.1 (M−H).

HPLC (method A): 3.484 min.

Synthesis of methyl 5-cyano-5-(4-nitrophenyl)-2-oxocyclohexanecarboxylate (3)

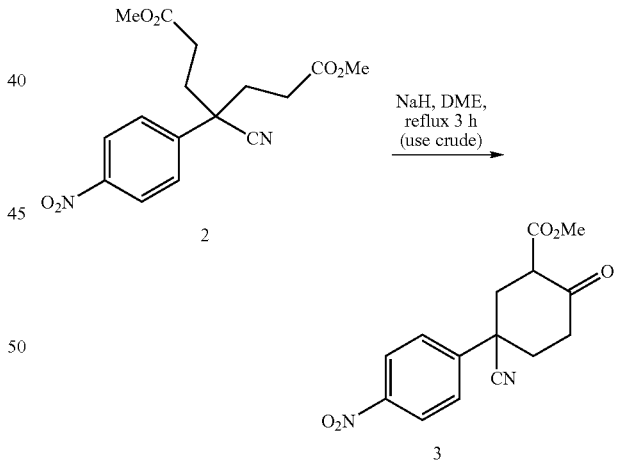

To a solution of 2 (88.96 g, 0.27 mol) in DME (1 L) at RT under $N_2$ was added (carefully) NaH (60% in mineral oil, 31.92 g, 0.80 mol) to give a dark violet solution. The reaction was heated at reflux for 4 h, was cooled and quenched carefully with $H_2O$, acidified with 2N HCl and extracted with 2×EtOAc. The combined organics were washed with saturated NaCl solution, dried over a mixture of activated charcoal and $Na_2SO_4$, filtered through Celite and evaporated to give crude product 3 as a brown solid (83.42 g, >100%).

$^1$H-NMR (500 MHz, dmso-$d_6$) 12.1 (s, 1H), 8.31 (d, 2H), 7.88 (d, 2H), 3.75 (s, 3H), 2.86 (AB quartet, 2H), 2.65 (m, 1H), 2.6 (m, 1H), 2.4 (m, 1H), 2.35 (m, 1H) ppm.

MS-FIA: 301.1 (M−H).
HPLC (method A): 3.729 min.

Synthesis of 1-(4-nitrophenyl)-4-oxocyclohexanecarbonitrile

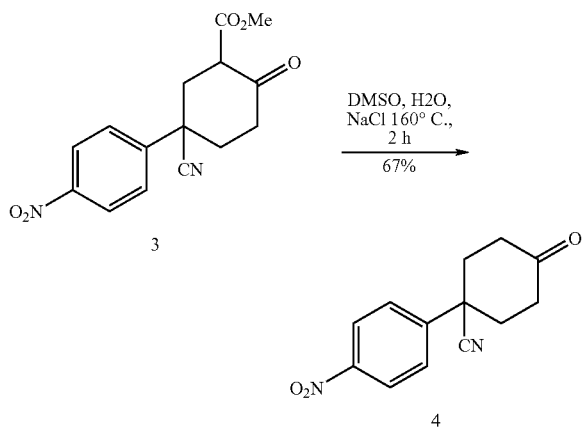

Crude 3 (0.27 mol), NaCl (80 g, 1.37 mol) and water (80 mL) were heated in DMSO (1.2 L) at 150-160° C. for 3 h. The solvent was distilled off, the residue was diluted with $H_2O$ and extracted with 3×EtOAc. The combined organics were washed with 2N HCl, 3×$H_2O$, NaCl solution, and dried over $Na_2SO_4$ and evaporated. Purification by flash chromatography (1 L $SiO_2$) eluted with 1:3, then 1:2 EtOAc:hexanes provided pure product 4 as an off-white solid (36.47 g, 56% yield), as well as very slightly impure product 4 as a greenish solid (14.33 g, 22% yield).

$^1$H-NMR (500 MHz, dmso-$d_6$) 8.31 (d, 2H), 7.92 (d, 2H), 2.74 (m, 2H), 2.5 (m, 6H) ppm.

MS-FIA: 243.2 (M−H).
HPLC (Method A): 3.121 min.

Synthesis of 4-morpholino-1-(4-nitrophenyl)cyclohexanecarbonitrile (5a)

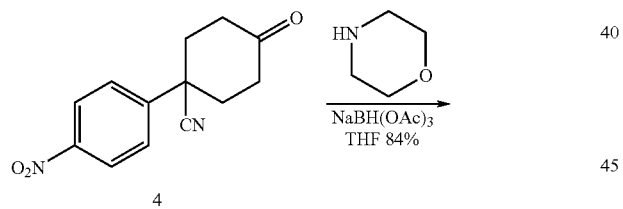

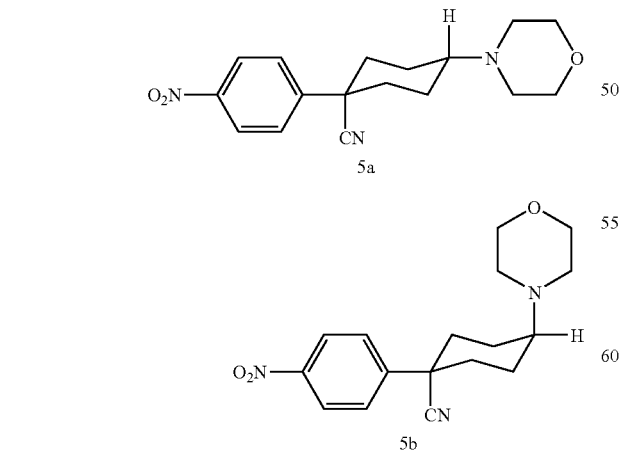

To a solution of 1-(4-nitrophenyl)-4-oxocyclohexanecarbonitrile (45.8 g, 187 mmol) in anhydrous THF (560 mL) at RT was added morpholine (17.2 mL, 197 mmol). The solution was stirred for 45 mins, then placed in a water bath at RT. Sodium triacetoxyborohydride (55.5 g, 260 mmol) was added portionwise over 10 mins. After 2.5 h the solvent was removed in vacuo, the mixture dissolved in EtOAc (400 mL) and extracted with 2N NaOH (3×75 mL). HCl gas was then bubbled through the organic phase to give a precipitate which was filtered, washed with EtOAc (2×) and $Et_2O$ (3×). The solid was dried under vacuum at 40° C. for 18 h to give a mixture of isomers (5a and 5c, 54.9 g, 84% yield).

Purification of isomer 5a (necessary for preparation of example 2; not necessary for preparation of example 1):

A mixture of 5a and 5b (79.4 g) was dissolved in $CH_2Cl_2$ (200 mL) and applied onto $SiO_2$ (2 L) which had been loaded into a 3 L fritted glass funnel. Elution was with 13 L of 1:1 ethyl acetate:hexanes into 1 L flasks to obtain a mixture of 5a and 5b (19.77 g, 25% recovery) as a pale yellow solid. Pure isomer 5a was obtained by further elution with 8 L of 5:95 methanol: $CH_2Cl_2$ to provide 57 g (72% recovery).

5a: $^1$H-NMR (500 MHz, dmso-$d_6$) 8.28 (d, 2H), 7.84 (d, 2H), 3.59 (m, 4H), 2.52 (m, 4H), 2.40 (tt, 1H), 2.18 (d, 2H), 2.02 (m, 4H), 1.60 (m, 2H) ppm. MS-FIA 316.1 (M+H). HPLC (method B) 2.537 min (100%).

5b: $^1$H-NMR (500 MHz, dmso-$d_6$) 8.30 (d, 2H), 7.82 (d, 2H), 3.59 (m, 4H), 2.38 (m, 4H), 2.28 (d, 2H), 2.26 (m, 1H), 1.94 (m, 4H), 1.74 (m, 2H) ppm. MS-FIA 316.1 (M+H). HPLC: 2.449 min (100%).

Synthesis of trans- and cis-4-(4-morpholin-4-yl-cyclohexyl)-phenylamine (6a and 6b)

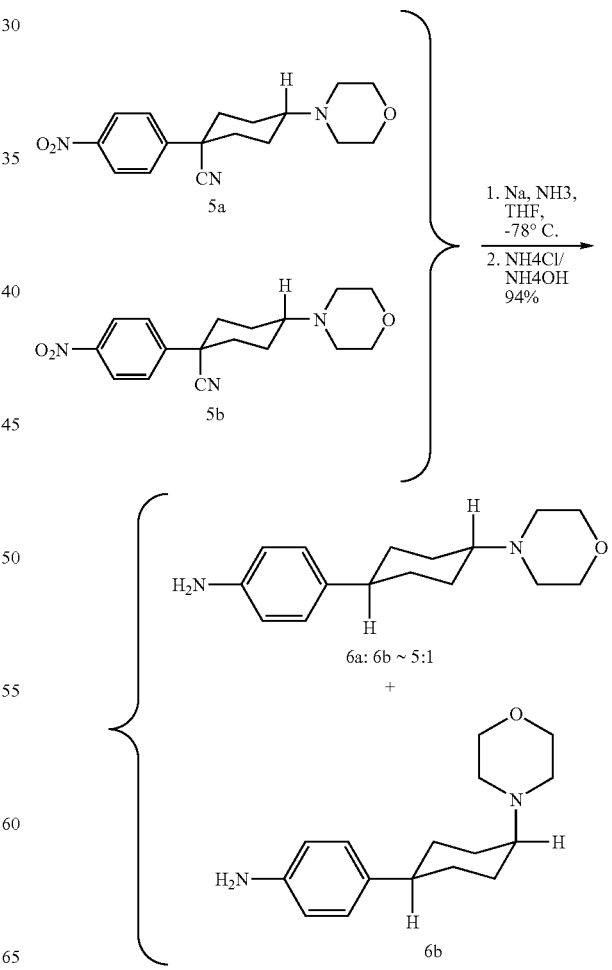

(References: S. B. Christensen e al, J. Med. Chem., 1998, 41, 821-835; and J. A. Marshall, et al, J. Org. Chem., 1977, 42, 3309-3311)

A 2 L, 3-necked round bottomed flask equipped with overhead mechanical stirrer, Claisen adapter with addition funnel (1 L) and dry-ice condenser was flame dried under nitrogen and allowed to cool. The condenser was charged with dry-ice/2-propanol and the flask cooled to −78 with dry-ice/2-propanol while under positive nitrogen pressure. Ammonia (1 L) gas was condensed while under nitrogen. The solution was then charged with 26.6 g (1.16 mol) of sodium metal. After 30 min a solution of 30 g (0.0951 mol) of 4-morpholino-1-(4-nitrophenyl)cyclohexanecarbonitrile in anhydrous THF (300 mL) was added drop-wise via addition funnel over 10 minutes. After complete addition, 50 mL of THF was used to rinse the funnel of any residual 4-morpholino-1-(4-nitrophenyl)cyclohexanecarbonitrile and the reaction allowed to warm to −33 and stir 5 hours. The reaction was quenched by drop-wise addition of NH4Cl/NH4OH (9/1, 100 mL) while under positive nitrogen pressure. Water (200 mL) then EtOAc (350 mL) was added and the ammonia allowed to evaporate while stirring overnight. The resulting suspension was filtered through celite and the aqueous layer extracted with EtOAc (3×200 mL). The combined organic layers were dried over MgSO4, filtered and concentrated under reduced pressure (rotovap) to give a mixture of 6a: 6b~5:1 as a pale yellow solid after vacuum drying at RT. (23.87 g., 96.4% yield). $^1$H-NMR (500 MHz, dmso-$d_6$) For 6a: 6.84 (d, 2H), 6.46 (d, 2H), 3.55 (m, 4H), 2.48 (m, 4H), 2.25 (tt, 1H), 2.22 (tt, 1H), 1.88 (d, 2H), 1.78 (d, 2H), 1.34 (m, 4H) ppm; Discernable peaks for 6b: 6.86 (d, 2H), 6.49 (d, 2H), 3.60 (m, 4H), 2.37 (m, 4H) ppm.

MS-FIA 261.2 (M+H).

Synthesis of (Z)-3-(4-(4-morpholinocyclohexyl)phenyl)-2-phenylisour

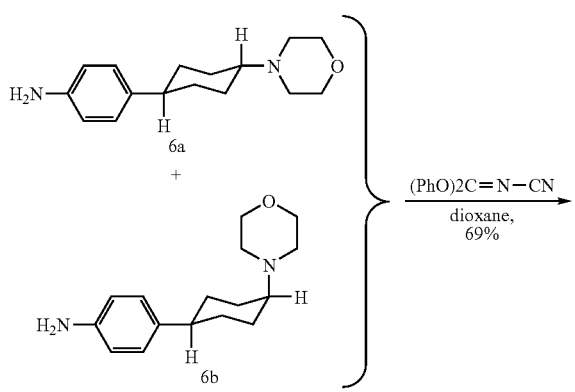

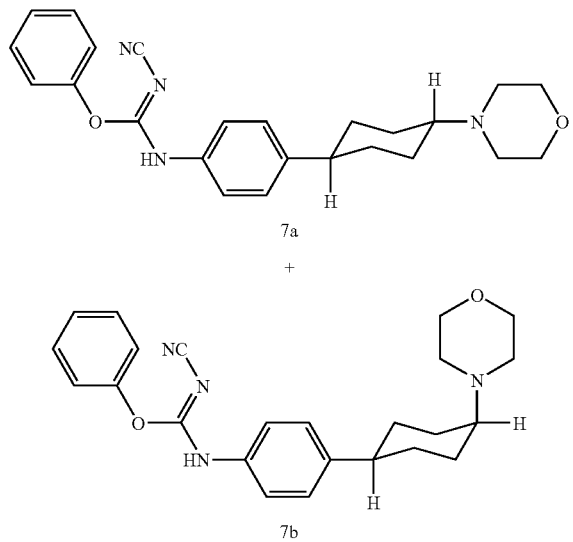

A mixture of cis- and trans-4-(4-morpholin-4-yl-cyclohexyl)-phenylamine 6b and 6a (20.28 g, 77.9 mmol) and diphenylcyanocarbonimidate (20.44 g, 85.6 mmol) in dioxane (350 mL) was stirred under $N_2$ for 4 days. The reaction was evaporated, then diluted with water and extracted with 5 portions (200 mL) of $CH_2Cl_2$. The combined organic phase was washed with $NaHCO_3$ and evaporated to dryness to provide a dark brown viscous oil. Trituration with $Et_2O$ (300 mL) gave a tan solid, which was further washed with 2 portions of $Et_2O$ (150 mL) to provide product 7a as a tan solid (21.70 g, 69%). $^1$H-NMR (500 MHz, dmso-$d_6$) 10.7 (br s, 1H), 7.44 (t, 2H), 7.35 (d, 2H), 7.25 (m, 5H), 3.57 (m, 4H), 2.51 (m, 4H), 2.44 (tt, 1H), 2.30 (m, 1H), 1.92 (d, 2H), 1.85 (d, 2H), 1.45 (m, 2H), 1.34 (m, 2H) ppm.

LC/MS (545% $CH_3CN$) 405.1 (M+H), 403.2 (M−H), $t_R$=3.4 min.

HPLC: 2.798 min.

Synthesis of N3-[4-(4-Morpholin-4-yl-cyclohexyl)-phenyl]-1-pyridin-2-yl-1H-[1,2,4]triazole-3,5-diamine

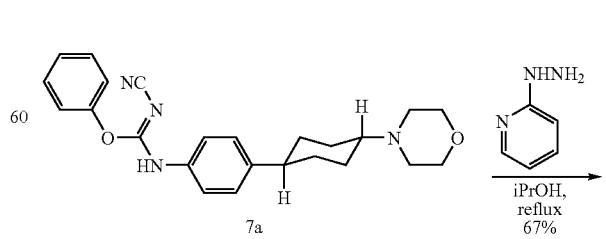

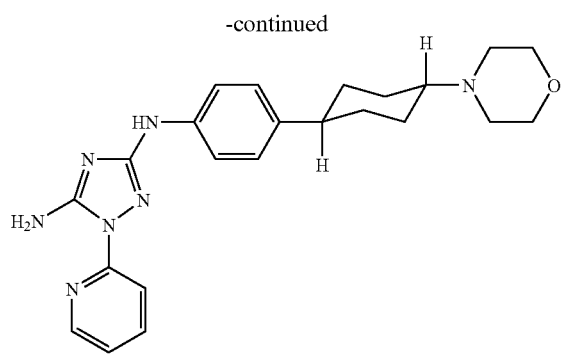

A solution of (Z)-3-(4-(4-morpholinocyclohexyl)phenyl)-2-phenylisourea 7a (7.00 g, 17.3 mmol) and 2-pyridylhydrazine (2.27 g, 20.8 mmol) was refluxed in iso-propanol (100 mL) for 2 days. The reaction was cooled, filtered and the resultant solid was washed with ethanol. The precipitate was recrystallized from dioxane, the crystals were filtered, suspended in methanol with stirring for 1 h, evaporated and dried at 60° C. under high vacuum for 3d. This provided pure I-3 (4.88 g, 67% yield) as a white solid.

$^1$H-NMR (500 MHz, dmso-$d_6$) 8.92 (s, 1H), 8.40 (m, 1H), 7.97 (m, 1H), 7.68 (d, 1H), 7.63 (s, 2H), 7.51 (d, 2H), 7.20 (m, 1H), 7.09 (d, 2H), 3.57 (m, 4H), 2.50 (m, 4H), 2.37 (tt, 1H), 2.26 (tt, 2H), 1.91 (d, 2H), 1.84 (d, 2H), 1.43 (m, 2H), 1.33 (m, 2H) ppm.

LC/MS (5-95% $CH_3CN$) 420.0 (M+H), $t_R$=30.1 min.
HPLC: 2.602 min.

Synthesis of N3-[4-(4-morpholin-4-yl-cyclohexyl)-phenyl]-1-pyridin-2-yl-1H-[1,2,4]triazole-3,5-diamine, mesylate salt

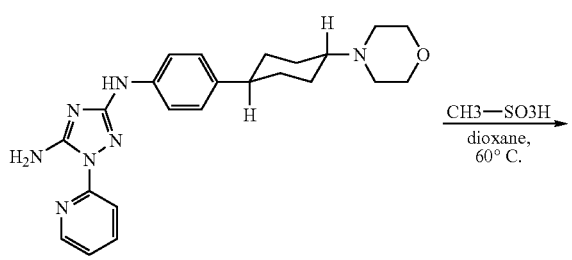

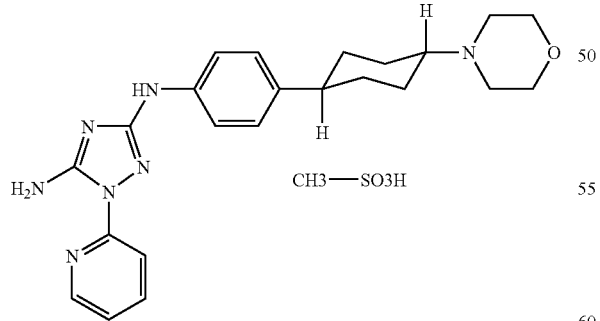

Example 1 (128.0 g, 0.305 mol) was suspended in dioxane (1.5 L) and heated at 60-70° C. Methanesulfonic acid (19.8 mL, 0.305 mol) was added dropwise over 10 min. Stirring continued for 1 h at 60-70° C. and 3 h at room temperature. The solid was filtered and washed with $Et_2O$, then 4 times suspended in methanol and evaporated before drying under high vacuum at 50-60° C. for 20 h. This suspension/evaporation/drying procedure was repeated once more with methanol, then once with ethanol in an unsuccessful attempt to rid the salt of traces of dioxane. The solid was suspended in water (1 L) and refluxed 15 min, then a centrifuge was used to separate the solid from the water. Centrifugation was repeated twice more. The wet solid was diluted with ethanol, evaporated and dried at 45-50° C. under high vacuum to provide 1-3, mesylate salt (129.95 g) as a white solid. The final product contains (by NMR) 0.3% dioxane.

$^1$H-NMR (500 MHZ, dmso-$d_6$) 9.51 (br s, 1H), 8.98 (s, 1H), 8.41 (m, 1H), 7.99 (m, 1H), 7.69 (d, 1H), 7.64 (s, 2H), 7.54 (d, 2H), 7.21 (m, 1H), 7.11 (d, 2H), 4.02 (d, 2H), 3.72 (t, 2H), 3.44 (d, 2H), 3.28 (m, 1H), 3.14 (m, 2H), 2.46 (m, 1H), 2.34 (s, 3H), 2.19 (m, 2H), 1.95 (m, 2H), 1.53 (m, 4H) ppm.

LC/MS (5-95% $CH_3CN$) 420.1 (M+H), $t_R$=3.2 min.
HPLC: 2.593 min.

Example 2

1-(4-(5-Amino-1-(pyridin-2-yl)-1H-1,2,4-triazol-3-ylamino)phenyl-4-morpholinocyclohexane carbonitrile

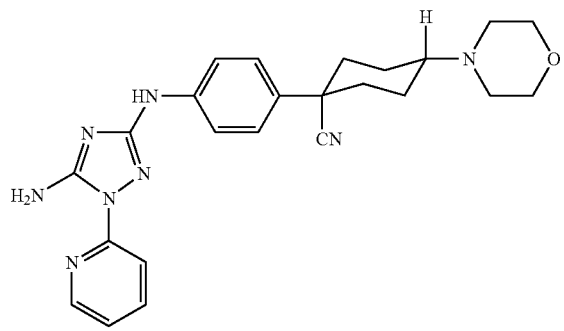

Synthesis of (Z)-1-cyano-3-(4-((1s,4s)-1-cyano-4-morpholinocyclohexyl)phenyl)-2-phenylisourea (6)

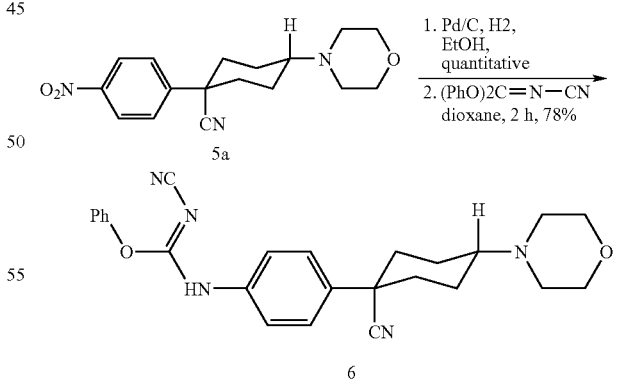

Intermediate 5a was prepared as described in Example 1. Trans-4-morpholino-1-(4-nitrophenyl)cyclohexanecarbonitrile, (20 g, 63.5 mmol), and 10% Pd—C catalyst (750 mg) in 250 mL ethanol were placed under hydrogen (38 psi) in a Parr shaker for 2 hours. Dichloromethane, 200 mL, was added to dissolve the product and the catalyst was filtered off. The solvents were evaporated to afford trans-1-(4-amino-phenyl)-

4-morpholin-4-yl-cyclohexanecarbonitrile (18.1 g, 63.5 mmol) as a pure yellow-tan solid which was used without further purification.

NMR CDCl3:7.25 (m, 2H), 6.70 (m, 2H), 3.7 (m, 6H), 2.65 (m, 4H), 2.35 (m, 1H), 2.25 (m, 2H), 2.05 (m, 2H), 1.85 (m, 4H), FIA MS m+1, 286.0

HPLC: method 10-90% $CH_3CN$: 2.488 min 100%

A solution of afford trans-1-(4-amino-phenyl)-4-morpholin-4-yl-cyclohexane carbonitrile (18.1 g, 63.5 mmol) and diphenyl cyanocarbonimidate (18.1 g, 76.2 mmol) was stirred in 1,4-dioxane (140 mL) at RT for 24 h. Distilled water (200 mL) was added to afford a white precipitate which was filtered and washed with water (100 mL), saturated sodium bicarbonate solution (150 mL), and water (200 mL). The solid was dried in a dessicator under vacuum overnight, to give the title compound 6 (21.1 g, 78% yield). 1H-NMR (DMSO, 500 MHz) 7.55 (m, 4H), 7.45 (m, 2H), 7.3 (m, 3H), 3.6 (m, 4H), 2.45 (m, 4H), 2.37 (t, 1H), 2.15 (d, 2H), 2.0 (d, 2H), 1.9 (t, 2H), 1.6 (m, 2H)]

MS+ 430.18, MS− 428.13, HPLC Rt=4.652 min (conditions 10-90% Acetonitrile over 7.5 min.

Synthesis of 1-(4-(5-Amino-1-(pyridin-2-yl)-1H-1,2,4-triazol-3-ylamino)phenyl-4-morpholinocyclohexane carbonitrile

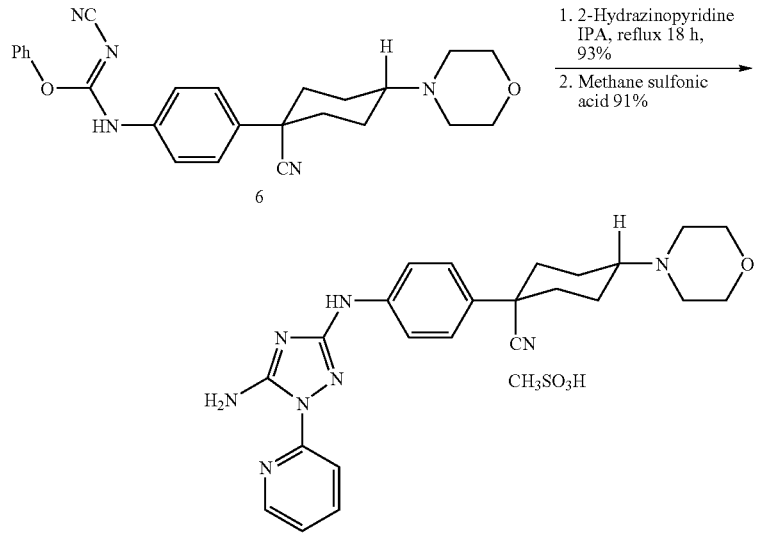

1-(4-(5-amino-1-(pyridin-2-yl)-1H-1,2,4-triazol-3-ylamino)phenyl-4-morpholinocyclohexane carbonitrile, (73 g, 0.164 mol), was added to dioxane (1 L) and the mixture warmed to 60-70° C. Methane sulfonic acid, (15.8 g, 0.164 mol) was added dropwise over 10 min. The heating bath was removed and the suspension allowed to stir for 3 hours. Isopropanol (200 mL) was added and the mixture filtered. The salt was washed with isopropanol, (50 mL), followed by diethyl ether (200 mL). The solid was suspended in 10% methanol-dichloromethane (500 mL) and stirred for 18 hours. Isopropanol (100 mL) was added and the solid filtered, then washed with ether to obtain pure mesylate salt (1-4, mesylate salt) as a white solid (81 g, 91% yield).

NMR: DMSO-d6:9.70 (bs, 1H), 9.25 (s, 1H), 8.40 (s, 1H), 7.95 (m, 1H), 7.65 (m, 3H), 7.40 (m, 2H), 7.20 (m, 1H), 4.06 (m, 2H), 3.75 (m, 2H), 3.55 (m, 2H), 3.50 (bs, 1H), 3.35 (m, 1H), 3.15 (m, 2H), 2.32 (m, 7H), 1.90 (m, 2H), 1.80 (m, 2H).

FIA MS m+1 445.2

LC-MS m+1: 445.3 1.88 min method 10-90% CH3CN

HPLC: method 10-90% CH3CN: 4.2 min 100%

Compounds of formulae I, II and II may be prepared by methods substantially similar to those described herein by one having ordinary skill in the art.

Example 3

Analytical Data

A variety of other compounds of Formula I have been prepared by methods substantially similar to those described herein. Representative characterization data for these compounds is summarized in Table 1 below and includes HPLC, LC/MS (observed), retention time (RT) and $^1H$ NMR data. Compound numbers correspond to the compound numbers provided herein.

TABLE 1

| Cmpd # | LC/MS | RT | 1HNMR |
|---|---|---|---|
| I-1 | 420.10 | 3.10 | (500MHz, dmso-d6)9.01(s, 1H), 8.41(m, 1H), 7.97(m, 1H), 7.68(d, 1H), 7.65(s, 2H), 7.59(d, 2H), 7.23(d, 2H), 7.21(m, 1H), 3.98(d, 2H), 3.68(t, 2H), 3.49(d, 2H), 3.32(m, 1H), 3.04(m, 2H), 2.85(m, 1H), 2.11(m, 2H), 1.89(m, 2H), 1.75(m, 4H)ppm |
| I-2 | 445.00 | 3.20 | (500MHz, dmso-d6)9.21(s, 1H), 8.41)m, 1H), 7.98(m, 1H), 7.73(d, 1H), 7.67(m, 4H), 7.39(d, 2H), 7.21(m, 1H), 3.58(m, 4H), 2.38(m, 4H), 2.25(m, 3H), 1.89(m, 4H), 1.72(m, 2H)ppm |
| I-5 | 484.00 | 3.20 | (dmso-d6, 500MHz)9.24(s, 1H), 8.42(m, 1H), 7.98(m, 1H), 7.71(d, 1H), 7.67(m, 4H), 7.40(d, 2H), 7.22(m, 1H), 3.53(m, 2H), 3.28(m, 1H), 3.16(m, 2H), 2.99(m, 2H), 2.66(d, 2H), 2.28(m, 4H), 1.91(m, |

TABLE 1-continued

| Cmpd # | LC/MS | RT | 1HNMR |
|---|---|---|---|
| | | | 3H), 1.78(m, 2H), 0.54(m, 2H), 0.45(m, 2H)ppm |
| I-6 | 486.20 | 2.05 | DMSO-d6: 8.90(s, 1H), 8.40(m, 1H), 7.98(m, 1H), 7.75(m, 1H), 7.65(s, 2H), 7.50(m, 2H), 7.20(m, 1H), 7.10(m, 2H), 4.02(s, 2H), 4.50(m, 2H), 4.40(m, 2H), 2.60(m, 1H), 2.45(m, 4H), 2.22(s, 1H), 2.1.85(m, 4H), 1.50(m, 4H). |
| I-7 | 459.10 | 3.10 | (500MHz, dmso-d6)9.00(s, 1H), 8.41(m, 1H), 7.97(m, 1H), 7.68(d, 1H), 7.65(s, 2H), 7.58(d, 2H), 7.22(m, 3H), 3.50(m, 2H), 3.30(m, 1H), 3.08(m, 2H), 2.98(m, 2H), 2.85(m, 1H), 2.63(m, 2H), 2.12(m, 2H), 1.8(m, 7H), 0.50(m, 2H), 0.39(m, 2H)ppm |
| I-8 | 419.20 | 1.54 | DMSO-d6: 8.95(s, 1H), 8.40(m, 1H), 7.95(m, 1H), 7.68(m, 1H), 7.60(bs, 2H), 7.55(m, 2H), 7.20(m, 1H), 7.10(m, 2H), 5.1(vbs, 1H), 2.85(m, 4H), 4.60(m, 1H), 2.50(m, 4H), 2.20(m, 1H), 1.90(m, 2H), 1.80(m, 2H), 1.45(m, 4H). |
| I-9 | 459.10 | 3.10 | (500MHz, dmso-d6)8.98(s, 1H), 8.40(m, 1H), 7.97(m, 1H), 7.68(d, 1H), 7.64(s, 2H), 7.53(d, 2H), 7.19(m, 1H), 7.09(d, 2H), 3.45(m, 2H), 3.26(m, 1H), 3.10(m, 2H), 2.99(m, 2H), 2.63(m, 3H), 2.15(m, 2H), 1.93(d, 2H), 1.81(m, 1H), 1.50(m, 4H), 0.50(m, 2H), 0.39(m, 2H)ppm |
| I-10 | 447.20 | 1.74 | MeOH-d4: 8.40(m, 1H), 7.90(m, 1H), 7.75(m, 1H), 7.50(m, 2H), 7.15(m, 3H), 3.5-2.5(m, 10H), 2.0(m, 4H), 1.70(m, 4H), 1.30(t, 3H). |
| I-11 | 418.00 | 2.20 | (500MHz, dmso-d6)8.98(s, 1H), 8.42-8.39(m, 1H), 8.00-7.93(m, 1H), 7.73-7.59(m, 3H), 7.56(d, 2H), 7.24-7.16(m, 1H), 7.11(d, 2H), 3.40(d, 2H), 3.29-3.17(m, 1H), 3.05-2.91(m, 2H), 2.45(m, 1H), 2.11(m, 2H), 1.93(d, 2H), 1.85(d, 2H), 1.76-1.34(m, 8H)ppm |
| I-12 | 483.00 | 3.10 | (500MHz, dmso-d6)8.93(s, 1H), 7.94(d, 2H), 7.79(d, 2H), 7.48(d, 2H), 7.08(d, 2H), 6.73(s, 2H), 3.44(m, 2H), 3.25(m, 2H), 3.05(m, 2H), 2.98(m, 1H), 2.58(m, 2H), 2.42(m, 1H), 2.15(m, 2H), 1.92(m, 2H), 1.75(m, 1H), 1.53(m, 4H), 0.47(m, 2H), 0.35(m, 2H)ppm |
| I-13 | 561.10 | 2.00 | DMSO-d6: 10.60(bs, 1H); 9.10(bs, 1H); 8.38(d, 1H); 7.80-8.20(bs, 2H); 7.48(d, 2H); 7.30(m, 2H); 6.62(m, 1H); 3.30-4.10(m, 15H); 3.00(m, 2H); 2.78(m, 1H); 2.20(m, 2H); 1.62-1.98(m, 11H) |
| I-14 | 586.10 | 2.00 | DMSO-d6: 9.35(s, 1H); 9.20(bs, 1H); 8.35(d, 1H); 7.78(bs, 2H); 7.70(d, 2H); 7.48(d, 2H); 6.62(d, 1H); 3.50-4.00(m, 10H); 3.40-3.50(m, 5H); 3.00(m, 2H); 2.72(m, 2H); 1.75-2.15(m, 9H); 1.52(m, 2H) |
| I-15 | 586.10 | 2.00 | DMSO-d6: 9.73(bs, 1H); 9.28(s, 1H); 8.35(d, 1H); 7.76(bs, 2H); 7.62(d, 2H); 7.35(d, 2H); 6.62(d, 1H); 3.55-4.08(m, 10H); 3.25-3.55(m, 5H); 3.15(m, 2H); 2.32(m, 4H); 1.75-2.15(m, 9H) |
| I-16 | 561.10 | 2.10 | DMSO-d6: 9.60(bs, 1H); 9.05(s, 1H); 8.35(d, 1H); 7.78(bs, 2H); 7.50(d, 2H); 7.08(d, 2H); 6.60(d, 1H); 3.50-4.10(m, 11H); 3.45(m, 4H); 3.25(m, 1H); 3.15(m, 2H); 2.12(m, 2H); 1.70-2.00(m, 7H); 1.50(m, 4H) |

Example 4

Inhibition of FLT-3

Compounds were screened for their ability to inhibit FLT-3 activity using a radiometric filter-binding assay. This assay monitors the $^{33}$P incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM $MgCl_2$, 25 mM NaCl, 1 mg/ml pE4Y and 180 µM ATP (containing 0.3 µCi of [γ-$^{33}$P] ATP for each reaction). Solution 2 contains 100 mM HEPES (pH7.5), 10 mM $MgCl_2$, 25 mM NaCl, 2 mM DTT, 0.02% BSA and 3 nM FLT-3. The assay was run on a 96 well plate by mixing 50 µL each of Solution 1 and 2.5 mL of the test compounds. The reaction was initiated with Solution 2. After incubation for 20 minutes at room temperature, the reaction was stopped with 50 µL of 20% TCA containing 0.4 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an $IC_{50}$ or $K_i$.

Compounds of the invention are effective for the inhibition of FLT-3.

Example 5

Inhibition of c-KIT

Compounds were screened for their ability to inhibit c-KIT activity using a radiometric filter-binding assay. This assay monitors the $^{33}$P incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 700 µM ATP and 0.5 mg/mL pE4Y (both from Sigma Chemicals, St Louis, Mo.). The final concentration of compounds is generally between 0.01 and 5 mM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM $MgCl_2$, 25 mM NaCl, 1 mg/ml pE4Y and 1.4 mM ATP (containing 0.5 µCi of [γ-$^{33}$P] ATP for each reaction). Solution 2 contains 100 mM HEPES (pH7.5), 10 mM $MgCl_2$, 25 mM NaCl, 2 mM DTT, 0.02% BSA and 25 nM c-KIT. The assay was run on a 96 well plate by mixing 33 µL of Solution 1 and 1.65 µL of the test compounds. The reaction was initiated with 33 µL of Solution 2. After incubation for 20 minutes at room temperature, the reaction was stopped with 50 µL of 10% TCA containing 0.2 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an $IC_{50}$ or $K_i$.

Compounds of the invention are effective for the inhibition of c-KIT.

Example 6

Inhibition of GSK-3

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30/g/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention are effective for the inhibition of GSK-3.

Example 7

Inhibition of CDK-2

Compounds were screened for their ability to inhibit CDK-2/Cyclin A using a standard coupled enzyme assay (Fox et al (1998) *Protein Sci* 7, 2249). Reactions were carried out in 100 mM HEPES pH 7.5, 10 mM $MgCl_2$, 25 mM NaCl, 1 mM DTT and 1.5% DMSO. Final substrate concentrations in the assay were 100 µM ATP (Sigma chemicals) and 100 µM peptide (American Peptide, Sunnyvale, Calif.). Assays were carried out at 30° C. and 25 nM CDK-2/Cyclin A. Final concentrations of the components of the coupled enzyme system were 2.5 mM phosphoenolpyruvate, 350 µM NADH, 30 µg/ml pyruvate kinase and 10 µg/ml lactate dehydrogenase.

An assay stock buffer solution was prepared containing all of the reagents listed above, with the exception of CDK-2/Cyclin A, DTT and the test compound of interest. 56 µl of the test reaction was placed in a 384 well plate followed by addition of 1 µl of 2 mM DMSO stock containing the test compound (final compound concentration 30 µM). The plate was preincubated for ~10 minutes at 30° C. and the reaction initiated by addition of 10 µl of enzyme (final concentration 25 nM). Rates of reaction were obtained using a BioRad Ultramark plate reader (Hercules, Calif.) over a 5 minute read time at 30° C. $K_i$ values were determined according to standard methods.

Compounds of the invention are effective for the inhibition of CDK-2.

Example 8

Inhibition of SRC

The compounds are evaluated as inhibitors of human Src kinase using either a radioactivity-based assay or spectrophotometric assay.

Src Inhibition Assay A: Radioactivity-Based Assay

The compounds are assayed as inhibitors of full-length recombinant human Src kinase (from Upstate Biotechnology, cat. no. 14-117) expressed and purified from baculo viral cells. Src kinase activity is monitored by following the incorporation of $^{33}$P from ATP into the tyrosine of a random poly Glu-Tyr polymer substrate of composition, Glu:Tyr=4:1 (Sigma, cat. no. P-0275). The following are the final concentrations of the assay components: 0.05 M HEPES, pH 7.6, 10 mM $MgCl_2$, 2 mM DTT, 0.25 mg/ml BSA, 10 µM ATP (1-2 loci $^{33}$P-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}$P-ATP. After 20 min of reaction, the reactions are quenched with 150 µl of 10% trichloroacetic acid (TCA) containing 20 mM $Na_3PO_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM $Na_3PO_4$ and then 4 times with methanol. 200 µl of scintillation fluid is then added to each well. The plates were sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quantified using a coupled enzyme assay (Fox et al (1998) *Protein Sci* 7, 2249). In this assay one molecule of NADH is oxidised to NAD for every molecule of ADP produced in the kinase reaction. The disappearance of NADH is conveniently followed at 340 nm.

The following are the final concentrations of the assay components: 0.025 M HEPES, pH 7.6, 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

Compounds of the invention are effective for the inhibition of SRC.

Example 9

Inhibition of SYK

Compounds were screened for their ability to inhibit Syk using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM Syk. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of Syk, DTT and the test compound of interest. 56 µl of the test reaction was placed in a 96 well plate followed by the addition of 1 µl of 2 mM DMSO stock containing the test compound (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C., and $K_i$ values were determined according to standard methods.

Compounds of the invention are effective for the inhibition of SYK.

Example 10

Inhibition of FMS

Compounds were screened for their ability to inhibit FMS activity using a radiometric filter-binding assay. This assay monitors the $^{33}P$ incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 mM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM $MgCl_2$, 25 mM NaCl, 1 mg/ml pE4Y and 180 FM ATP (containing 0.3 µCi of [γ-$^{33}P$] ATP for each reaction). Solution 2 contains 100 mM HEPES (pH7.5), 10 mM $MgCl_2$, 25 mM NaCl, 2 mM DTT, 0.02% BSA and 3 nM FMS. The assay was run on a 96 well plate by mixing 50 µL each of Solution 1 and 2.5 mL of the test compounds. The reaction was initiated with Solution 2. After incubation for 20 minutes at room temperature, the reaction was stopped with 50 µL of 20% TCA containing 0.4 mM of ATP. All of the reaction volume was then transferred to a filter plate and washed with 5% TCA by a Harvester 9600 from TOMTEC (Hamden, Conn.). The amount of $^{33}P$ incorporation into pE4y was analyzed by a Packard TopCount Microplate Scintillation Counter (Meriden, Conn.). The data was fitted using Prism software to get an $IC_{50}$ or $K_i$.

Compounds of the invention are effective for the inhibition of FMS.

Example 11

Rock Inhibition Assay

Compounds were screened for their ability to inhibit ROCK I (AA 6-553) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 2 mM DTT and 1.5% DMSO. Final substrate concentrations in the assay were 45 µM ATP (Sigma Chemicals, St Louis, Mo.) and 200 µM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 µM NADH, 30 µg/ml pyruvate kinase and 10 µg/ml lactate dehydrogenase.

Certain compounds of the invention were found to inhibit ROCK.

Example 12

JAK3 Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 µM ATP, 5 mM $MgCl_2$, and a solution of compound in DMSO. The reaction was started with JAK enzyme and the plates incubated for 60 minutes at 30° C. The plates were then washed with PBST, 100 µL HRP-Conjugated 4G10 antibody was added, and the plate incubated for 90 minutes at 30° C. The plate was again washed with PBST, 100 µL TMB solution is added, and the plates were incubated for another 30 minutes at 30° C. Sulfuric acid (100 µL of 1M) was added to stop the reaction and the plate is read at 450 nm to obtain the optical densities for analysis to determine $K_i$ values.

Compounds of the invention are effective for the inhibition of JAK-3.

Example 13

PDK-1 Inhibition Assay

Compounds were screened for their ability to inhibit PDK-1 using a radioactive-phosphate incorporation assay (Pitt and Lee, J. Biomol. Screen., (1996) 1, 47). Assays were carried out in a mixture of 100 mM HEPES (pH 7.5), 10 mM $MgCl_2$, 25 mM NaCl, 2 mM DTT. Final substrate concentrations in the assay were 40 µM ATP (Sigma Chemicals) and 65 µM peptide (PDKtide, Upstate, Lake Placid, N.Y.). Assays were carried out at 30° C. and 25 nM PDK-1 in the presence of ~27.5 nCi/µL of [γ-$^{32}P$]ATP (Amersham Pharmacia Biotech, Amersham, UK). An assay stock buffer solution was prepared containing all of the reagents listed above, with the exception of ATP, and the test compound of interest. 15 µl of the stock solution was placed in a 96 well plate followed by addition of 1 µl of 0.5 mM DMSO stock containing the test compound (final compound concentration 25 µM, final DMSO concentration 5%). The plate was preincubated for about 10 minutes at 30° C. and the reaction initiated by addition of 4 μl ATP (final concentration 40 μM).

The reaction was stopped after 10 minutes by the addition of 100 μL 100 mM phosphoric acid, 0.01% Tween-20. A phosphocellulose 96 well plate (Millipore, Cat no. MAPH-NOB50) was pretreated with 100 μL 100 mM phosphoric acid, 0.01% Tween-20 prior to the addition of the reaction mixture (100 μL). The spots were left to soak for at least 5 minutes, prior to wash steps (4×200 μL 100 mM phosphoric acid, 0.01% Tween-20). After drying, 20 μL Optiphase 'SuperMix' liquid scintillation cocktail (Perkin Elmer) was added to the well prior to scintillation counting (1450 Microbeta Liquid Scintillation Counter, Wallac).

Compounds showing greater than 50% inhibition versus standard wells containing the assay mixture and DMSO without test compound were titrated to determine $IC_{50}$ values.

Compounds of the invention are effective for the inhibition of PDK-1.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

The invention claimed is:

1. A compound of formula (I):

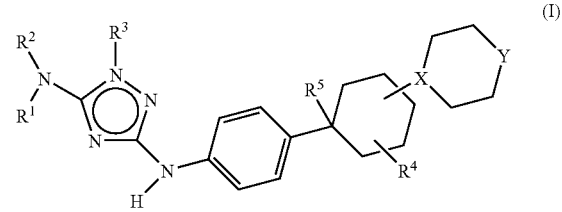

(I)

X is CH or N;
Y is $CH_2$, NH, NR, O, or S;
$R^1$ is hydrogen or $C_{1-6}$alkyl;
$R^2$ is hydrogen;
$R^3$ is an optionally substituted 6-membered aryl ring having 0-3 nitrogen heteroatoms;
$R^5$ is hydrogen, $-C_{1-6}$aliphatic, $-CN$, $-OH$, $-O(C_{1-6}$ aliphatic), $-CO_2H$, $-CO_2(C_{1-6}$aliphatic), $-CON(R)_2$, $-O(haloC_{1-4}$aliphatic), $-haloC_{1-4}$aliphatic, $-NO_2$, -halogen, $-NR°_2$, or $-C_{1-6}$aliphatic optionally substituted with $NH_2$;
$R^4$ is hydrogen, halogen; $-R°$; $-OR°$; $-SR°$; 1,2-methylenedioxy; 1,2-ethylenedioxy; phenyl (Ph) optionally substituted with $R°$; $-O(Ph)$ optionally substituted with $R°$; $-(CH_2)_{1-2}(Ph)$ optionally substituted with $R°$; $-CH=CH(Ph)$ optionally substituted with $R°$; $-NO_2$; $-CN$; $-N(R°)_2$; $-NR°C(O)R°$; $-NR°C(S)R°$; $-NR°C(O)N(R°)_2$; $-NR°C(S)N(R°)_2$; $-NR°CO_2R°$; $-NR°NR°C(O)R°$; $-NR°NR°C(O)N(R°)_2$; $-NR°NR°CO_2R°$; $-C(O)C(O)R°$; $-C(O)CH_2C(O)R°$; $-CO_2R°$; $-C(O)R°$; $-C(S)R°$; $-C(O)N(R°)_2$; $-C(S)N(R°)_2$; $-C(=NH)-N(R°)_2$, $-OC(O)N(R°)_2$; $-OC(O)R°$; $-C(O)N(OR°)R°$; $-C(NOR°)R°$; $-S(O)_2R°$; $-S(O)_3R°$; $-SO_2N(R°)_2$; $-S(O)R°$; $-NR°SO_2N(R°)_2$; $-NR°SO_2R°$; $-N(OR°)R°$; $-C(=NH)-N(R°)_2$; $-(CH_2)_{0-2}NHC(O)R°$, =O, =S, =NNHR*, =NN(R*)_2$, =NNHC(O)R*, =NNHCO_2(alkyl), =NNHSO_2(alkyl), or =NR*, wherein each independent occurrence of $R°$ is selected from hydrogen, optionally substituted $C_{1-6}$ aliphatic, an unsubstituted 5-6 membered heteroaryl or heterocyclic ring, phenyl, $-O(Ph)$, or $-CH_2(Ph)$, or, notwithstanding the definition above, two independent occurrences of $R°$, on the same substituent or different substituents, taken together with the atom(s) to which each $R°$ group is bound, form a 5-8-membered heterocyclyl, aryl, or heteroaryl ring or a 3-8-membered cycloalkyl ring having 0-3 heteroatoms independently selected from nitrogen, oxygen, or sulfur;

the aliphatic group of $R°$ is optionally substituted with $NH_2$, $NH(C_{1-4}$ aliphatic), $N(C_{1-4}$ aliphatic)_2$, halogen, $C_{1-4}$ aliphatic, $OH$, $O(C_{1-4}$ aliphatic), $NO_2$, $CN$, $CO_2H$, $CO_2(C_{1-4}$ aliphatic), $O(halo C_{1-4}$ aliphatic), or $halo(C_{1-4}$ aliphatic), wherein each of these foregoing $C_{1-4}$ aliphatic groups is unsubstituted;

each $R*$ is independently selected from hydrogen or a $C_{1-6}$ aliphatic optionally substituted with $NH_2$, $NH(C_{1-4}$ aliphatic), $N(C_{1-4}$ aliphatic)_2$, halogen, $C_{1-4}$ aliphatic, $OH$, $O(C_{1-4}$ aliphatic), $NO_2$, $CN$, $CO_2H$, $CO_2(C_{1-4}$ aliphatic), $O(halo C_{1-4}$ aliphatic), or $halo(C_{1-4}$ aliphatic), wherein each of these foregoing $C_{1-4}$ aliphatic groups is unsubstituted; and R is hydrogen or a $C_{1-6}$ aliphatic group, optionally substituted with =O, =S, $-NH_2$, $NH(C_{1-4}$ aliphatic), $N(C_{1-4}$ aliphatic)_2$, halogen, $C_{1-4}$ aliphatic, $OH$, $O(C_{1-4}$ aliphatic), $NO_2$, $CN$, $CO_2H$, $CO_2(C_{1-4}$ aliphatic), $O(halo C_{1-4}$ aliphatic), or $halo(C_{1-4}$ aliphatic), wherein each of these foregoing $C_{1-4}$ aliphatic groups is unsubstituted;

wherein each optional substituent of said aryl ring is independently selected from halogen; $-R°$; $-OR°$; $-SR°$; phenyl (Ph) optionally substituted with $R°$; $-O(Ph)$ optionally substituted with $R°$; $-(CH_2)_{1-2}(Ph)$, optionally substituted with $R°$; $-CH=CH(Ph)$, optionally substituted with $R°$; $-NO_2$; $-CN$; $-N(R°)_2$; $-NR°C(O)R°$; $-NR°C(S)R°$; $-NR°C(O)N(R°)_2$; $-NR°C(S)N(R°)_2$; $-NR°CO_2R°$; $-NR°NR°C(O)R°$; $-NR°NR°C(O)N(R°)_2$; $-NR°NR°CO_2R°$; $-C(O)C(O)R°$; $-C(O)CH_2C(O)R°$; $-CO_2R°$; $-C(O)R°$; $-C(S)R°$; $-C(O)N(R°)_2$; $-C(S)N(R°)_2$; $-OC(O)N(R°)_2$; $-OC(O)R°$; $-C(O)N(OR°)R°$; $-C(NOR°)R°$; $-S(O)_2R°$; $-S(O)_3R°$; $-SO_2N(R°)_2$; $-S(O)R°$; $-NR°SO_2N(R°)_2$; $-NR°SO_2R°$; $-N(OR°)R°$; $-C(=NH)-N(R°)_2$; $-P(O)_2R°$; $-PO(R°)_2$; $-OPO(R°)_2$; $-(CH_2)_{0-2}NHC(O)R°$; phenyl (Ph) optionally substituted with $R°$; $-O(Ph)$ optionally substituted with $R°$; $-(CH_2)_{1-2}(Ph)$, optionally substituted with $R°$; or $-CH=CH(Ph)$, optionally substituted with $R°$; notwithstanding the definition above, two independent occurrences of $R°$, on the same substituent or different substituents, taken together with the atom(s) to which each $R°$ group is bound, to form a 3-12 membered saturated, partially unsaturated, or fully unsaturated monocyclic or bicyclic ring having 0-4 heteroatoms independently selected from nitrogen, oxygen, or sulfur and optionally substituted with R.

2. The compound according to claim 1, wherein $R^1$ is hydrogen.

3. The compound according to claim 2, wherein $R^3$ is a 6 membered heteroaryl group having 1 or 2 nitrogen heteroatoms.

4. The compound according to claim 2, wherein $R^3$ is 2-pyridyl.

5. A compound according to claim 1, having the formula (I-b) or (I-c):
I-b
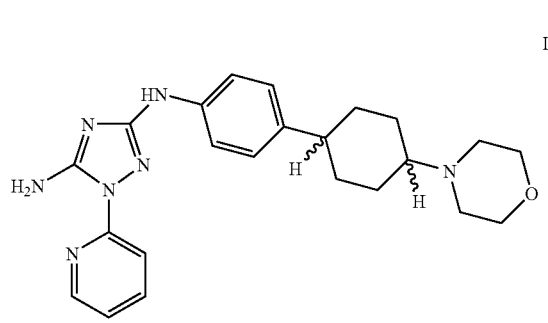
I-c
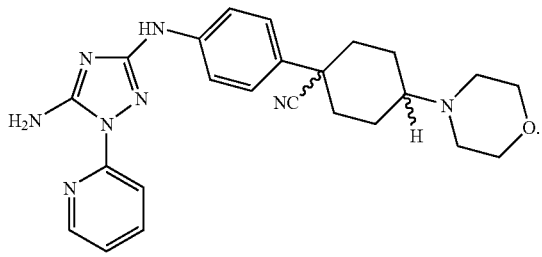
6. The compound according to claim 1, wherein said compound is selected from the group consisting of:
I-1
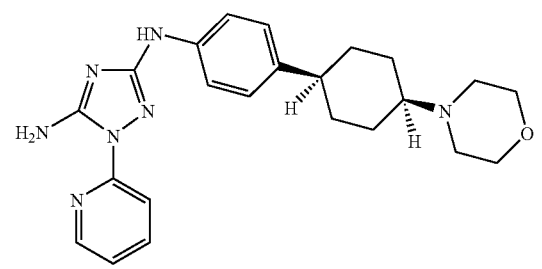
I-2
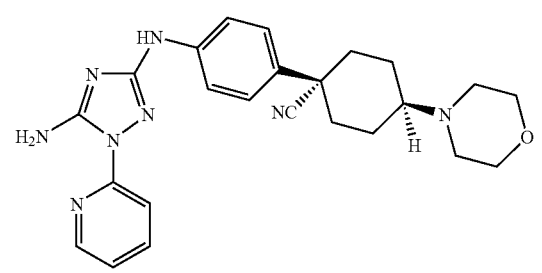
I-3
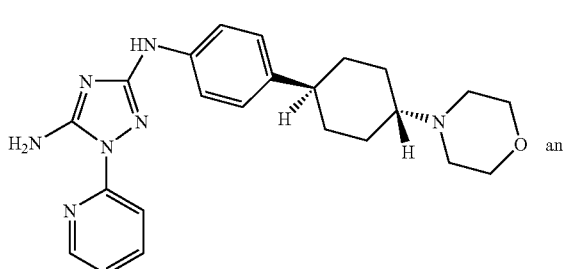
and
-continued
I-4
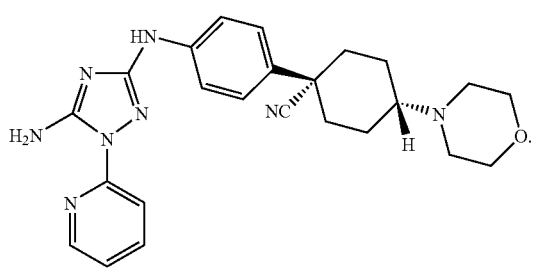
7. A compound according to claim 1, wherein said compound is selected from the group consisting of
I-5
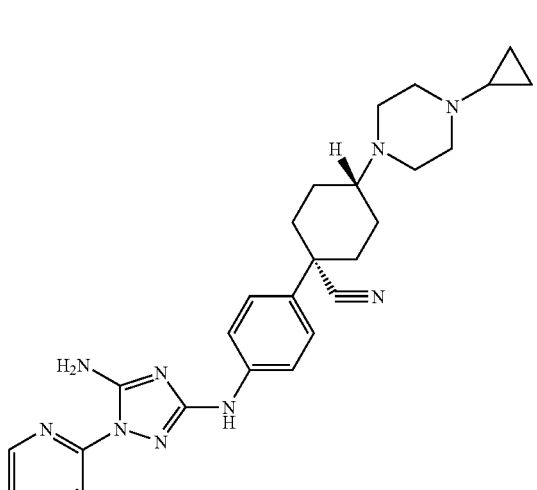
I-6

I-7
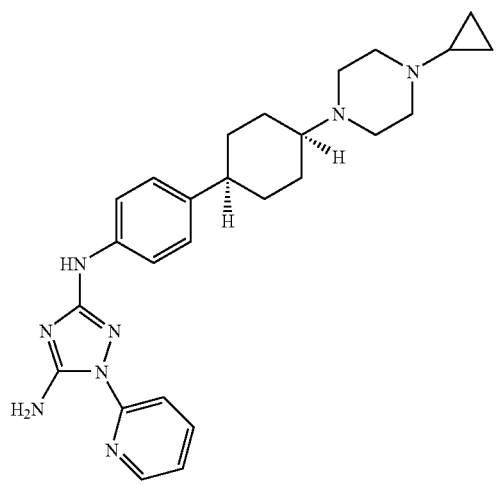
I-10
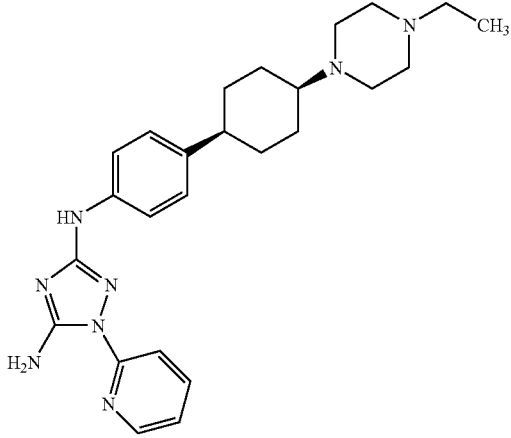
I-8
I-11
and
I-9
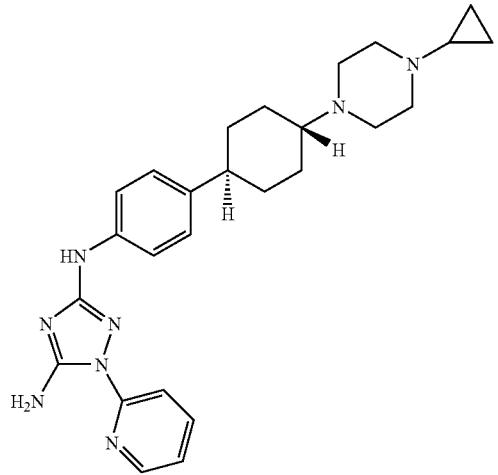
I-12
8. The compound according to claim 1, wherein said compound is selected from the group consisting of

I-13

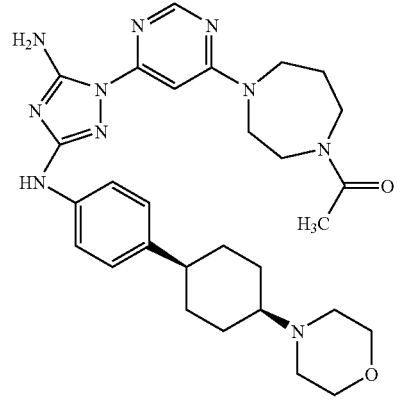

I-14

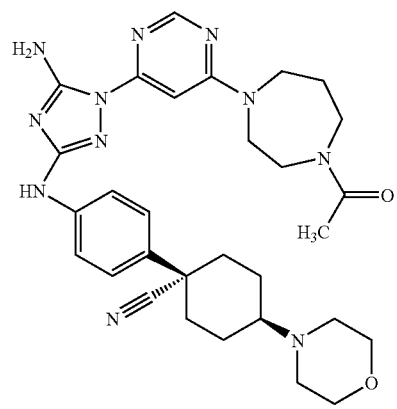

I-15

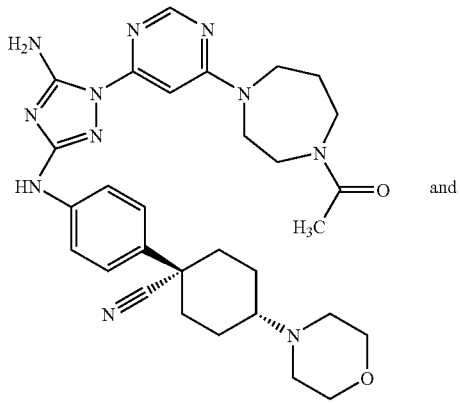

and

I-16

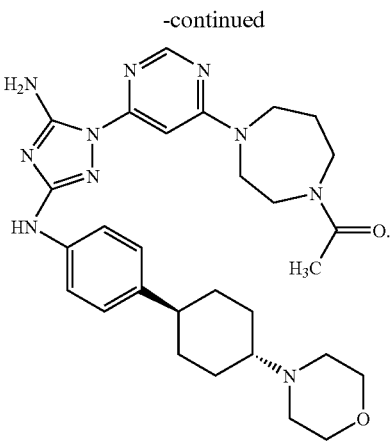

9. A pharmaceutical composition comprising:
a compound according to claim 1 or a pharmaceutically acceptable salt thereof, and a pharmaceutically acceptable carrier, adjuvant, or vehicle.

10. The composition of claim 9, further comprising a therapeutic agent selected from a chemotherapeutic or anti-proliferative agent, an agent for treating Alzheimer's Disease, an agent for treating Parkinson's Disease, an agent for treating Multiple Sclerosis (MS), an agent for treating asthma, an agent for treating schizophrenia, an anti-inflammatory agent, an immunomodulatory or immunosuppressive agent, a neurotrophic factor, an agent for treating cardiovascular disease, an agent for treating destructive bone disorders, an agent for treating liver disease, an agent for treating a blood disorder, or an agent for treating an immunodeficiency disorder.

11. A pharmaceutical composition comprising:
a compound according to claim 8 or a pharmaceutically acceptable salt thereof, and a pharmaceutically acceptable carrier, adjuvant, or vehicle.

12. A method of inhibiting FLT-3 or c-KIT kinase activity in a biological sample in vitro, comprising the step of contacting said biological sample with:
a) a compound according to claim 1 or a pharmaceutically acceptable salt thereof or
b) a composition of said compound or pharmaceutically acceptable salt thereof and a pharmaceutically acceptable carrier, adjuvant or vehicle.

* * * * *